United States Patent
Buschmann et al.

(10) Patent No.: US 10,130,629 B2
(45) Date of Patent: *Nov. 20, 2018

(54) PHARMACEUTICAL COMBINATIONS

(71) Applicant: Novartis AG, Basel (CH)

(72) Inventors: Nicole Buschmann, Basel (CH); Robin Alec Fairhurst, Basel (CH); Jorge Garcia Fortanet, Wilmington, MA (US); Pascal Furet, Thann (FR); Diana Graus Porta, Basel (CH); Nafeeza Hafeez, Brookline, MA (US); Bo Han, Shanghai (CN); Thomas Knoepfel, Rheinfelden (CH); Matthew J. LaMarche, Reading, MA (US); Catherine Leblanc, Basel (CH); Lv Liao, Shanghai (CN); Robert Mah, Muttenz (CH); Dale Porter, Cambridge, MA (US); Can Wang, Suzhou (CN); Markus Wartmann, Riehen (CH); Jing Xiong, Shanghai (CN); Xianglin Zhao, Shanghai (CN)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/561,209

(22) PCT Filed: Mar. 23, 2016

(86) PCT No.: PCT/IB2016/051634
§ 371 (c)(1),
(2) Date: Sep. 25, 2017

(87) PCT Pub. No.: WO2016/151501
PCT Pub. Date: Sep. 29, 2016

(65) Prior Publication Data
US 2018/0064709 A1 Mar. 8, 2018

(30) Foreign Application Priority Data
Mar. 25, 2015 (WO) ............... PCT/CN2015/075067

(51) Int. Cl.
*A61K 31/496* (2006.01)
*A61K 31/4439* (2006.01)
*A61K 31/497* (2006.01)
*A61K 31/506* (2006.01)
*A61K 31/519* (2006.01)
*A61K 31/5377* (2006.01)

(52) U.S. Cl.
CPC ........ *A61K 31/496* (2013.01); *A61K 31/4439* (2013.01); *A61K 31/497* (2013.01); *A61K 31/506* (2013.01); *A61K 31/519* (2013.01); *A61K 31/5377* (2013.01)

(58) Field of Classification Search
CPC .................................................. A61K 31/496
See application file for complete search history.

(56) References Cited

FOREIGN PATENT DOCUMENTS

| WO | 2006/000420 A1 | 1/2006 |
|---|---|---|
| WO | 2007/084786 A1 | 7/2007 |
| WO | 2010/020675 A1 | 2/2010 |
| WO | 2010/029082 A1 | 3/2010 |
| WO | 2011/071821 A1 | 6/2011 |
| WO | 2012/044727 A2 | 4/2012 |
| WO | 2012/064805 A1 | 5/2012 |
| WO | 2015/059668 A1 | 4/2015 |
| WO | 2015/107495 A1 | 7/2015 |

*Primary Examiner* — Craig D Ricci
(74) *Attorney, Agent, or Firm* — David Cheung

(57) ABSTRACT

A pharmaceutical combination comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, or a pharmaceutically acceptable salt thereof, and at least one active ingredient, as defined herein, or a pharmaceutically acceptable salt thereof, and optionally a pharmaceutically acceptable carrier, for simultaneous or sequential administration; the uses of such combination in the treatment of proliferative diseases; and methods of treating a subject suffering from a proliferative disease comprising administering a therapeutically effective amount of such combination.

7 Claims, 15 Drawing Sheets

Figure 1. Growth inhibition of HUH7 cells when treated with a concentration range of CPi and CPii-a after seven days of treatment.

Figure 2. Growth inhibition of HUH7 cells when treated with a concentration range of CPi and CPii-b after seven days of treatment.

Figure 3. Growth inhibition of HUH7 cells when treated with a concentration range of CPi and CPii-d after seven days of treatment.

Figure 4. Growth inhibition of HUH7 cells when treated with a concentration range of CPi and CPii-e after seven days of treatment.

Figure 5. Growth inhibition of HUH7 cells when treated with a concentration range of CPi and CPii-f after three days of treatment.

PHARMACEUTICAL COMBINATIONS

FIELD OF THE INVENTION

The present invention relates to a pharmaceutical combination comprising
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and
(ii) at least one further active ingredient, as defined herein, in free form or in pharmaceutically acceptable salt form, and optionally at least one pharmaceutically acceptable carrier; the uses of such a combination in the treatment or prevention of proliferative diseases, such as cancer, in particular liver cancer; and methods of treating a subject suffering from a proliferative disease, such as cancer, in particular liver cancer, comprising administering a therapeutically effective amount of such a combination.

BACKGROUND OF THE INVENTION

In spite of numerous treatment options for patients with cancer, there remains a need for effective and safe therapeutic agents and a need for new combination therapies that can be administered for the effective long-term treatment of cancer.

Liver cancer or hepatic cancer is classified as primary liver cancer (i.e. cancer that forms in the tissues of the liver) and secondary liver cancer (i.e. cancer that spreads to the liver from another part of the body). According to the National Cancer Institute at the National Institutes of Health, the number of estimated new cases and deaths from liver and intrahepatic bile duct cancer in the United States in 2014 was 33,190 and 23,000, respectively. Importantly, the percent surviving five years or more after being diagnosed with liver and intrahepatic bile duct cancer is only about 16%.

It has now been found that a combination of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and at least one further active ingredient, as defined herein, shows synergistic combination activity in an in vitro cell proliferation assay as shown in the experimental section and may therefore be effective for the delay of progression or treatment of a proliferative disease, such as cancer, in particular liver cancer.

Based on the synergistic combination activity shown in the experimental section, it would be expected that the combination of
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and
(ii) at least one further active ingredient selected from the group consisting of
   a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
   b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
   c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
   d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
   e) 4-(trifluoromethyl)-5-(2,6-dimorpholinopyrimidin-4-yl)pyridin-2-amine in free form or in pharmaceutically acceptable salt form, would result in an unexpected improvement in the treatment of proliferative diseases, particularly cancer, and more particularly liver cancer. This unexpected improvement would allow, for example, the reduction in the dose required for each compound, leading, for example, to a reduction in the side effects or an enhancement of the long-term clinical effectiveness of the compounds in treatment.

When administered simultaneously or sequentially, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and at least one further active ingredient, as defined herein, interact in a synergistic manner to strongly inhibit cell proliferation and would be thus surprisingly efficacious in liver cancer. This unexpected synergistic reaction would allow, for example, reduction in the dose required for each compound, leading, for example, to a reduction in the side effects or an enhancement of the long-term clinical effectiveness of the compounds in treatment.

SUMMARY OF THE INVENTION

The invention provides pharmaceutical combinations and therapeutic methods which may be useful for inhibiting the cell growth of a tumor and for treating proliferative diseases, particularly cancer, and more particularly liver cancer.

The present invention provides pharmaceutical combinations comprising:
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient, as defined herein, in free form or in pharmaceutically acceptable salt form and optionally at least one pharmaceutically acceptable carrier.

In the combinations of the present invention, the active ingredient in (ii) is selected from the group consisting of
   a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
   b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
   c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
   d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and e) 4-(trifluoromethyl)-5-(2,6-dimorpholinopyrimidin-4-yl)pyridin-2-amine in free form or in pharmaceutically acceptable salt form.

The present invention further relates to a combined preparation or a pharmaceutical composition comprising
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
　a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
　b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
　c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
　d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
　e) 4-(trifluoromethyl)-5-(2,6-dimorpholinopyrimidin-4-yl)pyridin-2-amine in free form or in pharmaceutically acceptable salt form,
and optionally at least one pharmaceutically acceptable carrier. In one embodiment, the present invention relates to a combined preparation which comprises: (1) one or more unit dosage forms of combination partner (i), as defined herein, and (2) one or more unit dosage forms of combination partner (ii), as defined herein.

The present invention particularly pertains to a pharmaceutical combination comprising
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
　a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
　b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
　c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
　d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
　e) 4-(trifluoromethyl)-5-(2,6-dimorpholinopyrimidin-4-yl)pyridin-2-amine in free form or in pharmaceutically acceptable salt form,
and optionally at least one pharmaceutically acceptable carrier for use in the treatment or prevention of a proliferative disease, such as cancer, in particular liver cancer, in a subject in need thereof.

The present invention also pertains to a pharmaceutical combination comprising
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
　a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
　b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
　c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
　d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
　e) 4-(trifluoromethyl)-5-(2,6-dimorpholinopyrimidin-4-yl)pyridin-2-amine in free form or in pharmaceutically acceptable salt form,
and optionally at least one pharmaceutically acceptable carrier for use in the manufacture of a pharmaceutical composition or medicament for the treatment or prevention of a proliferative disease, such as cancer, in particular liver cancer, in a subject in need thereof.

The present invention further pertains to the use of
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
　a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
　b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
　c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
　d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
　e) 4-(trifluoromethyl)-5-(2,6-dimorpholinopyrimidin-4-yl)pyridin-2-amine in free form or in pharmaceutically acceptable salt form,
for the manufacture of a pharmaceutical composition or medicament for the treatment or prevention of a proliferative disease, such as cancer, in particular liver cancer.

The present invention relates to a method of treating a proliferative disease, such as cancer, in particular liver cancer, in a subject in need thereof, comprising the simultaneous or sequential administration to said subject of a therapeutically effective amount of
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form,
in combination with
(ii) at least one further active ingredient selected from the group consisting of
  a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
  b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
  c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
  d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
  e) 4-(trifluoromethyl)-5-(2,6-dimorpholinopyrimidin-4-yl)pyridin-2-amine in free form or in pharmaceutically acceptable salt form,
and optionally at least one pharmaceutically acceptable carrier.

In an embodiment, the invention relates to a method of treating a proliferative disease, such as cancer, in particular liver cancer, in a subject in need thereof, comprising the simultaneous or sequential administration of a therapeutically effective amount of
(i) the citrate salt or the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide,
in combination with
(ii) at least one further active ingredient selected from the group consisting of
  a) the monophosphate salt of 3-(2,6-dichloro-3,5-dimethoxy-phenyl)-1-{6-[4-(4-ethyl-piperazin-1-yl)-phenylamino]-pyrimidin-4-yl}-1-methyl-urea;
  b) the free form of 8-(6-amino-5-((2-(trifluoromethyl)pyridin-3-yl)thio)pyrazin-2-yl)-8-azaspiro[4.5]decan-1-amine;
  c) the succinate salt of 7-Cyclopentyl-2-(5-piperazin-1-yl-pyridin-2-ylamino)-7H-pyrrolo[2,3-d]pyrimidine-6-carboxylic acid dimethylamide;
  d) the free form of (S)-N1-(4-methyl-5-(2-(1,1,1-trifluoro-2-methylpropan-2-yl)pyridin-4-yl)thiazol-2-yl)pyrrolidine-1,2-dicarboxamide; and
  e) the hydrochloride salt of 4-(trifluoromethyl)-5-(2,6-dimorpholinopyrimidin-4-yl)pyridin-2-amine.

The present invention further provides a commercial package comprising a pharmaceutical combination comprising
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
  a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
  b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
  c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
  d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
  e) 4-(trifluoromethyl)-5-(2,6-dimorpholinopyrimidin-4-yl)pyridin-2-amine in free form or in pharmaceutically acceptable salt form,
together with instructions for simultaneous or sequential administration thereof for use in the delay of progression or treatment of a proliferative disease, such as cancer, in particular liver cancer.

The above combinations are also provided for use as a medicament, in particular for use in treating or preventing a proliferative disease, such as cancer, in particular liver cancer.

DETAILED DESCRIPTION OF THE INVENTION

Figure 1A:
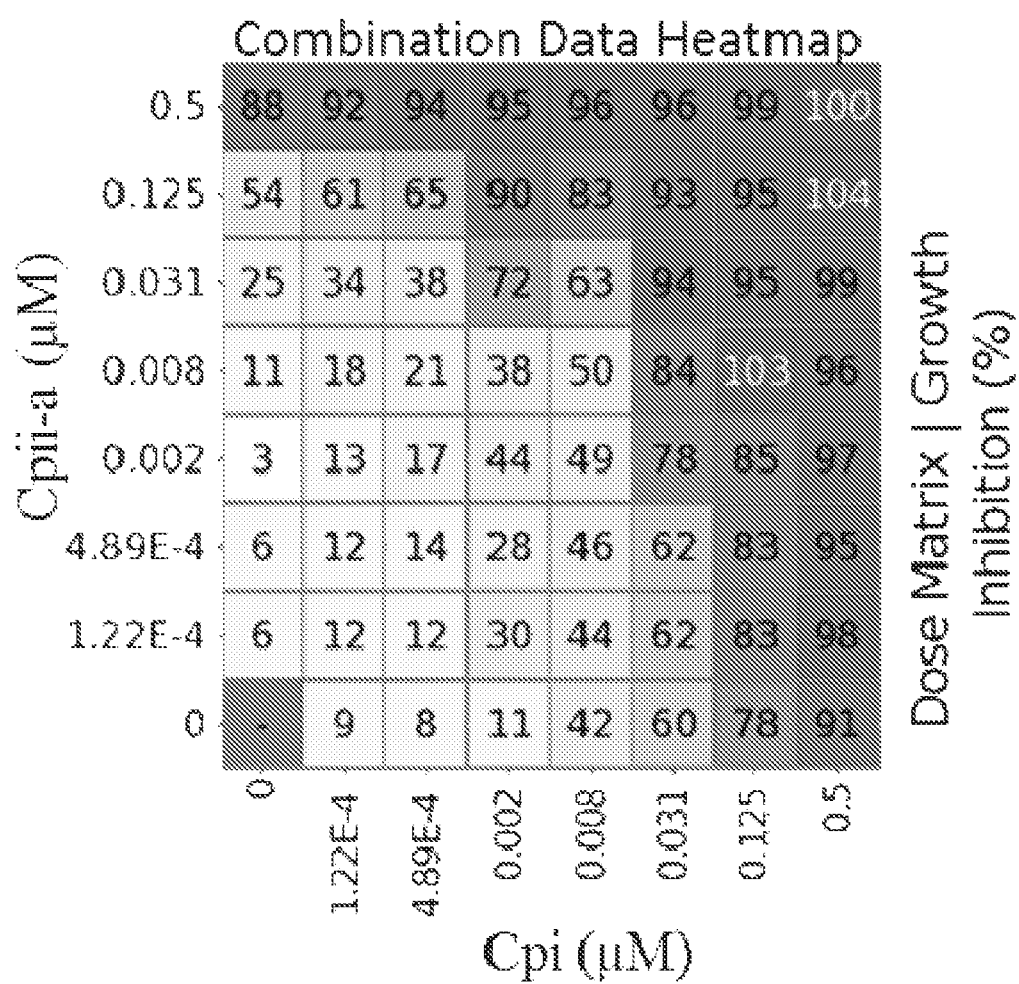
FIG. 1. Growth inhibition of HUH7 cells when treated with a concentration range of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated as CPi) and 3-(2,6-dichloro-3,5-dimethoxy-phenyl)-1-{6-[4-(4-ethyl-piperazin-1-yl)-phenylamino]-pyrimidin-4-yl}-1-methyl-urea monophosphate salt (abbreviated as CPii-a) after seven days of treatment.

The present invention provides pharmaceutical combinations comprising:
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient, as defined herein, in free form or in pharmaceutically acceptable salt form and optionally at least one pharmaceutically acceptable carrier.

Thus, a pharmaceutical combination which comprises (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) at least one further active ingredient, as defined herein, or pharmaceutically acceptable salt thereof, and optionally at least one pharmaceutically acceptable carrier, will be referred to herein as a COMBINATION OF THE INVENTION. This term is also taken to mean a pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) one further active ingredient, as defined herein, as the sole active ingredients.

The present invention provides pharmaceutical combinations comprising:
(i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and
(ii) at least one further active ingredient selected from the group consisting of
  a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
  b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
  c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
  d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
  e) 4-(trifluoromethyl)-5-(2,6-dimorpholinopyrimidin-4-yl)pyridin-2-amine in free form or in pharmaceutically acceptable salt form,
and optionally at least one pharmaceutically acceptable carrier.

The present invention relates to such pharmaceutical combinations for use as a medicament, in particular for use in the treatment or prevention of a proliferative disease, such as cancer, in particular liver cancer.

A combination of the invention, as defined herein, could be effective for the delay of progression or treatment of a proliferative disease, such as cancer, particularly liver cancer. In particular, a combination, as defined herein, could result, for example, in an unexpected improvement, over monotherapy, in the treatment of proliferative diseases, particularly cancer, and more particularly liver cancer. This unexpected improvement would allow, for example: a reduction in the dose required or dose frequency for ACTIVE INGREDIENT (i) [i.e. N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form]; a reduction in the dose required or dose frequency for ACTIVE INGREDIENT (ii), as defined herein; a reduction in the dose required or dose frequency for both ACTIVE INGREDIENTS (i) and (ii), as defined herein; a reduction in the side effects of ACTIVE INGREDIENT (i), (ii) or both, as defined herein; an improved quality of life or a decreased morbidity; or an enhancement of the long-term clinical effectiveness for ACTIVE INGREDIENT (i), (ii) or both, as defined herein; as compared with monotherapy applying only one of the active ingredients used in the combination of the invention. Preferably, the combination of the invention would provide a synergistic therapeutic effect, e.g. with regard to alleviating, delaying progression of or inhibiting the symptoms of proliferative diseases, such as cancer, particularly liver cancer.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" as used herein refers to either a fixed combination in one unit dosage form (e.g. capsule, tablet or sachet), a non-fixed combination or a kit of parts for the combined administration where N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form [i.e. ACTIVE INGREDIENT (i)], and at least one further active ingredient [e.g. ACTIVE INGREDIENT (ii)], as defined herein, or a pharmaceutically acceptable salt thereof, may be administered simultaneously, independently at the same time or separately within time intervals that allow the combination partners to show a cooperative, e.g., synergistic effect. The term "fixed combination" means that the active ingredients, i.e. ACTIVE INGREDIENT (i), as defined herein, and one or more combination partners [i.e. ACTIVE INGREDIENT (ii), as defined herein], are administered to a patient simultaneously in the form of a single entity or unit dosage form. The term "non-fixed combination" means that the active ingredients, i.e. ACTIVE INGREDIENT (i), as defined herein, and one or more combination partners [i.e. ACTIVE INGREDIENT (ii), as defined herein], are administered to a patient as separate entities either simultaneously or sequentially with no specific time limits, wherein such administration provides therapeutically effective levels of the two compounds in the body of the patient. This applies to combinations of two active ingredients and also to a cocktail therapy, e.g. the administration of three or more active ingredients.

The term "a combined preparation" is defined herein to refer to especially "a kit of parts" in the sense that the combination partners [i.e. ACTIVE INGREDIENT (i) and ACTIVE INGREDIENT (ii)] as defined herein can be dosed independently or by use of different fixed combinations with distinguished amounts of the combination partners [e.g. ACTIVE INGREDIENT (i) and ACTIVE INGREDIENT (ii)], simultaneously or at different time points. The parts of the kit of parts can then e.g., be administered simultaneously or chronologically staggered, that is at different time points and with equal or different time intervals for any part of the kit of parts. The ratio of the total amounts of one combination partner to the other combination partner to be administered in the combined preparation can be varied, e.g., in order to cope with the needs of a patient sub-population to be treated or the needs of the single patient.

The term "at least one" when referring to ACTIVE INGREDIENT (ii) or to "further active ingredient" refers to one, two, three or four. Preferably, it is one.

According to the present invention, suitable combination partners (ii) [i.e. herein also referred to as ACTIVE INGREDIENT (ii)] include:
  a) 3-(2,6-dichloro-3,5-dimethoxy-phenyl)-1-{6-[4-(4-ethyl-piperazin-1-yl)-phenylamino]-pyrimidin-4-yl}-1-methyl-urea having the formula

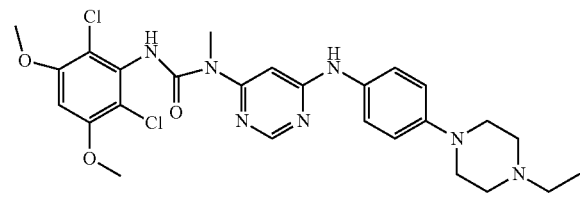 [SMILES: CCN1CCN(c2ccc(Nc3cc(N(C)C(=O)Nc4c(Cl)c(OC)cc(OC)c4Cl)ncn3)cc2)CC1]

(described in Example 145 in WO2006/000420) in free form or in pharmaceutically acceptable salt form, in particular in monophosphate salt form (described in Example 3 in WO2011/071821);
  b) 8-(6-amino-5-((2-(trifluoromethyl)pyridin-3-yl)thio)pyrazin-2-yl)-8-azaspiro[4.5]decan-1-amine having the formula

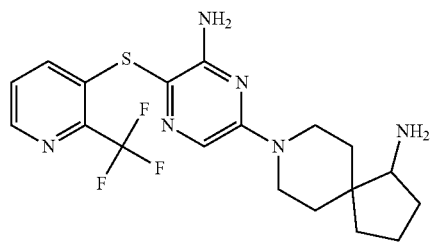 [SMILES: Nc1nc(N2CCC3(CCCC3N)CC2)cnc1Sc1cccnc1C(F)(F)F]

(described in Example 1 in PCT/IB2015/050345) in free form or in pharmaceutically acceptable salt form, in particular in free form;
  c) 7-Cyclopentyl-2-(5-piperazin-1-yl-pyridin-2-ylamino)-7H-pyrrolo[2,3-d]pyrimidine-6-carboxylic acid dimethylamide having the formula

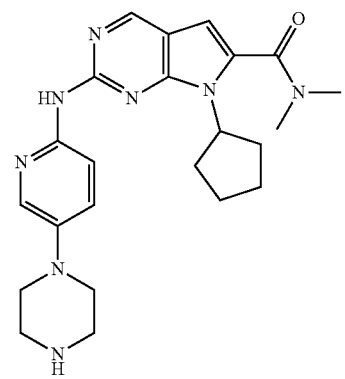 [SMILES: CN(C)C(=O)c1cc2cnc(Nc3ccc(N4CCNCC4)cn3)nc2n1C1CCCC1]

(described in Example 74 in WO2010/020675) and having also the following chemical name: 7-cyclopentyl-N,N-dimethyl-2-((5-(piperazin-1-yl)pyridin-2-yl)amino)-7H-pyrrolo[2,3-d]pyrimidine-6-carboxamide; in free from or in pharmaceutically acceptable salt form, in particular in succinate salt form (described in WO2012/064805);
  d) (S)-N1-(4-methyl-5-(2-(1,1,1-trifluoro-2-methylpropan-2-yl)pyridin-4-yl)thiazol-2-yl)pyrrolidine-1,2-dicarboxamide having the formula

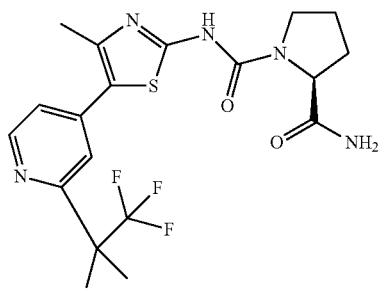 [SMILES: Cc1nc(NC(=O)N2CCC[C@H]2C(N)=O)sc1-c1ccnc(C(C)(C)C(F)(F)F)c1]

(described in Example 15 in WO2010/029082) in free form or in pharmaceutically acceptable salt form, in particular in free form;
  e) 4-(trifluoromethyl)-5-(2,6-dimorpholinopyrimidin-4-yl)pyridin-2-amine having the formula

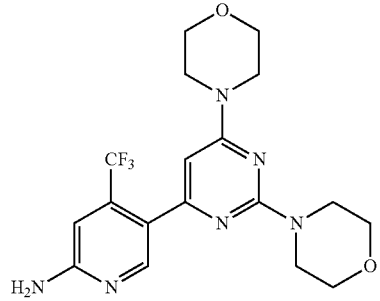

(described in Example 10 in WO2007/084786), and having also the following chemical names:
5-(2,6-di-morpholin-4-yl-pyrimidin-4-yl)-4-trifluoromethyl-pyridin2-ylamine, or
5-(2,6-di-4-morpholinyl-4-pyrimidinyl)-4-trifluoromethyl-pyridin-2-amine, or
5-(2,6-dimorpholinopyrimidin-4-yl)-4-(trifluoromethyl)pyridin-2-amine, or 5-(2,6-di-4-morpholinyl-4-pyrimidinyl)-4-(trifluoromethyl)-2-pyridinamine;
in free form or in pharmaceutically acceptable salt form, in particular the hydrochloride salt thereof (described in WO2012/044727).

The compound 8-(6-amino-5-((2-(trifluoromethyl)pyridin-3-yl)thio)pyrazin-2-yl)-8-azaspiro[4.5]decan-1-amine described above may be in the form of a racemate, in (R) form or in (S) form. In one embodiment, 8-(6-amino-5-((2-(trifluoromethyl)pyridin-3-yl)thio)pyrazin-2-yl)-8-azaspiro[4.5]decan-1-amine is a racemate. In one embodiment, 8-(6-amino-5-((2-(trifluoromethyl)pyridin-3-yl)thio)pyrazin-2-yl)-8-azaspiro[4.5]decan-1-amine is in (R) form as depicted below:

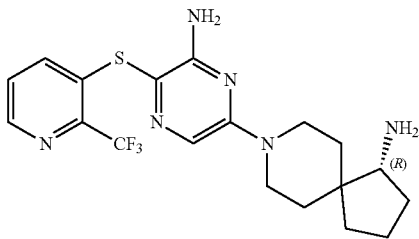

In one embodiment, 8-(6-amino-5-((2-(trifluoromethyl)pyridin-3-yl)thio)pyrazin-2-yl)-8-azaspiro[4.5]decan-1-amine is in (S) form as depicted below:

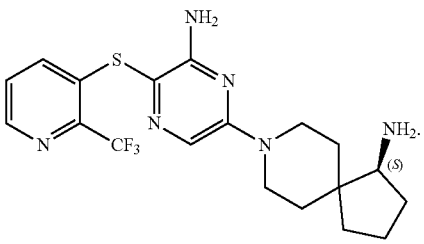

Each of the references cited above are incorporated herein by reference.

The term "pharmaceutical composition" is defined herein to refer to a mixture or solution containing at least one active ingredient or therapeutic agent to be administered to a subject, e.g., a mammal or human, in order to prevent or treat a particular disease or condition affecting the mammal or human, in particular a proliferative disease, such as cancer, particularly liver cancer.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "drug", "active substance", "active ingredient", "active agent", "agent" are to be understood as meaning a compound in free form or in the form of a pharmaceutically acceptable salt, in particular compounds specified herein. Herein, the term "ACTIVE INGREDIENT (i)" is also referred to as "combination partner (i)" and relates to N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form. Similarly, the term "ACTIVE INGREDIENT (ii)" is also referred to as "combination partner (ii)", and refers to any of a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;

b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;

c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;

d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and e) 4-(trifluoromethyl)-5-(2,6-dimorpholinopyrimidin-4-yl)pyridin-2-amine in free form or in pharmaceutically acceptable salt form.

The term "co-administration" or "combined administration" as used herein is defined to encompass the administration of the selected active ingredients to a single subject in need thereof (e.g. a patient), and are intended to include treatment regimens in which the agents are not necessarily administered by the same route of administration or at the same time.

The term "treat", "treating", "treatment" or "therapy" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human.

The term "prevent", "preventing" or "prevention" as used herein comprises the prevention of at least one symptom associated with or caused by the state, disease or disorder being prevented.

The term "jointly therapeutically effective amount" as used herein means the amount at which the therapeutic agents, when given separately (in a chronologically staggered manner, especially a sequence-specific manner) to a warm-blooded animal, especially to a human to be treated, show a (preferably synergistic) interaction (joint therapeutic effect). Whether this is the case can be determined inter alia by following the blood levels, showing that both compounds are present in the blood of the human to be treated at least during certain time intervals.

The term "pharmaceutically effective amount" of a combination of therapeutic agents is an amount sufficient to provide an observable improvement over the baseline observable signs and symptoms of the disorder treated with the combination.

The term "synergistic effect" as used herein refers to an effect of at least two therapeutic agents: the ACTIVE INGREDIENT (i), as defined herein, and at least one ACTIVE INGREDIENT (ii), as defined herein, which is greater than the simple addition of the effects of each drug administered by themselves. The effect can be, for example, slowing the symptomatic progression of a proliferative disease, such as cancer, particularly cancer liver, or symptoms thereof. A synergistic effect can be calculated as shown in the examples. Analogously, a "synergistically effective amount" refers to the amount needed to obtain a synergistic effect.

The term "subject" or "patient" as used herein includes animals, which are capable of suffering from or afflicted with a proliferative disease, such as a cancer or any disorder involving, directly or indirectly, a cancer, particularly liver cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from a proliferative disease, such as cancer, particularly liver cancer.

The term about" or "approximately" shall have the meaning of within 10%, more preferably within 5%, of a given value or range.

When referring to ACTIVE INGREDIENT (i), the term "salt" or "salts" is understood to be a salt of ACTIVE INGREDIENT (i) and are preferably pharmaceutically acceptable salts. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. A most preferred salt of the ACTIVE INGREDIENT (i) is the citrate salt. The stoichiometry of the citrate salt of ACTIVE INGREDIENT (i) is preferably 1:1 (citric acid: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide).

Except as otherwise indicated, the description or naming of a particular compound in the specification and claims is intended to include both individual enantiomers, diastereomeric mixtures, racemic or otherwise, thereof. Accordingly, this invention also includes all such isomers, including diastereomeric mixtures and resolved enantiomers of the compounds of this invention. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced organic Chemistry", $4^{th}$ edition, J. March. John Wiley and Sons, New York, 1992).

As related to the ACTIVE INGREDIENT (ii), the term "salt" or "salts", unless otherwise indicated, includes salts of acidic and basic groups which may be present in the ACTIVE INGREDIENT (ii). An ACTIVE INGREDIENT (ii) that is basic in nature is capable of forming a wide variety of salts with various inorganic and organic acids.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Since an ACTIVE INGREDIENT (ii) may include more than one acidic or basic moieties, the ACTIVE INGREDIENT (ii) may include mono, di or tri-salts in a single active ingredient. In the case of an acidic moiety in an ACTIVE INGREDIENT (ii), a salt may be formed by treatment of an ACTIVE INGREDIENT (ii) with a basic compound, particularly an inorganic base. For example, inorganic salts are those formed with alkali and alkaline earth metals such as lithium, sodium, potassium, barium and calcium. Organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, and salts formed with basic amino acids such as glycine, ornithine, histidine, phenylglycine, lysine and arginine. Preferred salts of ACTIVE INGREDIENT (ii) of the present invention are as defined herein.

Unless otherwise specified, or clearly indicated by the text, reference to therapeutic agents useful in the pharmaceutical combination of the present invention includes both the free form and all pharmaceutically acceptable salts of the ACTIVE INGREDIENT (i) and ACTIVE INGREDIENT (ii).

In each case where citations of patent applications are given above, the subject matter relating to the compounds is hereby incorporated into the present application by reference. The compounds used as therapeutic agents in the pharmaceutical combinations of the present invention can be prepared and administered as described in the cited documents, respectively. Also within the scope of this invention is the combination of two separate therapeutic agents as set forth above, i.e., a pharmaceutical combination within the scope of this invention could include three therapeutic agents or more.

In an embodiment, the combination of the invention is used for the treatment of a proliferative disease. In one embodiment, the proliferative disease is cancer. In particular, the cancer is selected from liver cancer, breast cancer, glioblastoma, prostate cancer, rhabdomyosarcoma, gastric cancer, ovarian cancer, lung cancer, colon cancer. More particularly, the cancer is liver cancer.

In an embodiment, the combination of the invention may also be useful in the treatment of solid malignancies characterized by positive FGFR4 expression.

In an embodiment, the combinations of the invention may also be useful in the treatment of solid malignancies characterized by positive KLB (beta-klotho) expression.

In an embodiment, the combinations of the invention may also be useful in the treatment of solid malignancies characterized by positive FGF19 expression.

In an embodiment, the combinations of the invention may also be useful in the treatment of solid malignancies characterized by positive FGFR4 and positive KLB expression.

In an embodiment, the combinations of the invention may also be useful in the treatment of solid malignancies characterized by positive FGFR4 and positive FGF19 expression.

In an embodiment, the combinations of the invention may also be useful in the treatment of solid malignancies characterized by positive FGFR4, positive KLB and positive FGF19 expression.

Any positive expression in FGFR4, KLB and/or FGF19 as described above can be assessed by methods known to the skilled person such as e.g. RT-qPCR, Western blotting, ELISA, immunohistochemistry.

The pharmaceutical compositions for separate administration of both combination partners, or for the administration in a fixed combination, i.e. a single galenical composition comprising the COMBINATION OF THE INVENTION, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers, especially suitable for enteral or parenteral application. The pharmaceutical composition may contain, from about 0.1% to about 99.9%, preferably from about 1% to about 60%, of the therapeutic agent(s). Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4th edition, Rowe et al., Eds., American Pharmaceuticals Association (2003); and *Remington: the Science and Practice of Pharmacy*, 20th edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight. Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In accordance with the present invention, a therapeutically effective amount of each of the combination partner, i.e. ACTIVE INGREDIENT (i) and ACTIVE INGREDIENT (ii), as defined herein, of the COMBINATION OF THE INVENTION may be administered simultaneously or sequentially and in any order, and the combination partners may be administered separately or as a fixed combination. For example, the method of treating a proliferative disease according to the invention may comprise (1) administration of the ACTIVE INGREDIENT (i) in free or pharmaceutically acceptable salt form and (2) administration of the ACTIVE INGREDIENT (ii) in free or pharmaceutically acceptable salt form, simultaneously or sequentially in any order, in jointly therapeutically effective amounts, preferably in synergistically effective amounts, e.g. in daily or intermittently dosages. The individual combination partners, i.e. ACTIVE INGREDIENT (i) and ACTIVE INGREDIENT (ii), as defined herein, of the COMBINATION OF THE INVENTION may be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the combination partners, i.e. ACTIVE INGREDIENT (i) and ACTIVE INGREDIENT (ii), as defined herein, of the COMBINATION OF THE INVENTION that yield efficacy without toxicity are based on the kinetics of the therapeutic agents' availability to target sites, and may be determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the COMBINATION OF THE INVENTION, are marketed as single drugs, their dosage and mode of administration can be in accordance with the information provided on the package insert of the respective marketed drug, if not mentioned herein otherwise.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking.

The amount of each combination partner that may be combined with the carrier materials to produce a unit dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

PREFERRED EMBODIMENTS

Various enumerated embodiments of the invention are described herein. It will be recognized that features specified in each embodiment may be combined with other specified features to provide further embodiments of the present invention.

Embodiment 1. A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) at least one further active ingredient selected from the group consisting of
a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
b) 8-(6-amino-5-((2-(trifluoromethyl)pyridin-3-yl)thio)pyrazin-2-yl)-8-azaspiro[4.5]decan-1-amine in free form or in pharmaceutically acceptable salt form;
c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
e) 4-(trifluoromethyl)-5-(2,6-dimorpholinopyrimidin-4-yl)pyridin-2-amine in free form or in pharmaceutically acceptable salt form.

Embodiment 2. A pharmaceutical combination according to embodiment 1, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3. A pharmaceutical combination according to embodiment 1, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 4. A pharmaceutical combination according to any of embodiments 1 to 3, wherein the active ingredient in (ii) is selected from the group consisting of
a) the monophosphate salt of 3-(2,6-dichloro-3,5-dimethoxy-phenyl)-1-{6-[4-(4-ethyl-piperazin-1-yl)-phenylamino]-pyrimidin-4-yl}-1-methyl-urea;
b) the free form of 8-(6-amino-5-((2-(trifluoromethyl)pyridin-3-yl)thio)pyrazin-2-yl)-8-azaspiro[4.5]decan-1-amine;
c) the succinate salt of 7-Cyclopentyl-2-(5-piperazin-1-yl-pyridin-2-ylamino)-7H-pyrrolo[2,3-d]pyrimidine-6-carboxylic acid dimethylamide;
d) the free form of (S)-N1-(4-methyl-5-(2-(1,1,1-trifluoro-2-methylpropan-2-yl)pyridin-4-yl)thiazol-2-yl)pyrrolidine-1,2-dicarboxamide; and
e) the hydrochloride salt of 4-(trifluoromethyl)-5-(2,6-dimorpholinopyrimidin-4-yl)pyridin-2-amine.

Embodiment 5. A pharmaceutical combination according to any of embodiments 1 to 4, wherein the active ingredient 8-(6-amino-5-((2-(trifluoromethyl)pyridin-3-yl)thio) pyrazin-2-yl)-8-azaspiro[4.5]decan-1-amine is in the form of a racemate.

Embodiment 6. A pharmaceutical combination according to any of embodiments 1 to 4, wherein the active ingredient 8-(6-amino-5-((2-(trifluoromethyl)pyridin-3-yl)thio) pyrazin-2-yl)-8-azaspiro[4.5]decan-1-amine is in (R) form.

Embodiment 7. A pharmaceutical combination according to any of embodiments 1 to 4, wherein the active ingredient 8-(6-amino-5-((2-(trifluoromethyl)pyridin-3-yl)thio) pyrazin-2-yl)-8-azaspiro[4.5]decan-1-amine is in (S) form.

Embodiment 8. A pharmaceutical combination according to any one of embodiments 1 to 7 further comprising at least one pharmaceutically acceptable carrier.

Embodiment 9. A pharmaceutical combination according to any one of the preceding embodiments, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the active ingredient(s) in (ii) in free form or in pharmaceutically acceptable salt form are the sole active ingredients.

Embodiment 10. A pharmaceutical combination according to any one of the preceding embodiments for use as a medicament.

Embodiment 11. A pharmaceutical combination according any one of the preceding embodiments for use in the treatment of a proliferative disease, such as cancer, in particular liver cancer.

Embodiment 12. Use of a pharmaceutical combination according to any one of embodiments 1 to 9 for the manufacture of a medicament for the treatment of a proliferative disease, such as cancer, in particular liver cancer.

Embodiment 13. Use of a pharmaceutical combination according to any one of embodiments 1 to 9 for the manufacture of a pharmaceutical composition for the treatment of a proliferative disease, such as cancer, in particular liver cancer.

Embodiment 14. A pharmaceutical combination according to any one of embodiments 1 to 9, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and the active ingredient(s) in (ii) in free form or in pharmaceutically acceptable salt form are provided in synergistically effective amounts for use in the treatment of a proliferative disease, such as cancer, in particular liver cancer.

Embodiment 15. A combined preparation comprising (1) one or more unit dosage forms of (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (2) one or more unit dosage forms of (ii) at least one further active ingredient selected from the group consisting of
a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
b) 8-(6-amino-5-((2-(trifluoromethyl)pyridin-3-yl)thio) pyrazin-2-yl)-8-azaspiro[4.5]decan-1-amine in free form or in pharmaceutically acceptable salt form;
c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
d) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form; and
e) 4-(trifluoromethyl)-5-(2,6-dimorpholinopyrimidin-4-yl) pyridin-2-amine in free form or in pharmaceutically acceptable salt form.

Embodiment 16. A combined preparation according to embodiment 15, wherein N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the active ingredient(s) in (ii) in free form or in pharmaceutically acceptable salt form are the sole active ingredients.

Embodiment 17. A combined preparation according to embodiment 15, wherein N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 18. A combined preparation according to embodiment 17, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and the active ingredient(s) in (ii) in free form or in pharmaceutically acceptable salt form are the sole active ingredients.

Embodiment 19. A combined preparation according to embodiment 15, wherein N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 20. A combined preparation according to embodiment 19, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and the active ingredient(s) in (ii) in free form or in pharmaceutically acceptable salt form are the sole active ingredients.

Embodiment 21. A combined preparation according to any of embodiments 15 to 20 wherein the active ingredient in (ii) is selected from the group consisting of
a) the monophosphate salt of 3-(2,6-dichloro-3,5-dimethoxy-phenyl)-1-{6-[4-(4-ethyl-piperazin-1-yl)-phenylamino]-pyrimidin-4-yl}-1-methyl-urea;
b) the free form of 8-(6-amino-5-((2-(trifluoromethyl)pyridin-3-yl)thio)pyrazin-2-yl)-8-azaspiro[4.5]decan-1-amine;
c) the succinate salt of 7-Cyclopentyl-2-(5-piperazin-1-yl-pyridin-2-ylamino)-7H-pyrrolo[2,3-d]pyrimidine-6-carboxylic acid dimethylamide;
d) the free form of (S)-N1-(4-methyl-5-(2-(1,1,1-trifluoro-2-methylpropan-2-yl)pyridin-4-yl)thiazol-2-yl)pyrrolidine-1,2-dicarboxamide; and
e) the hydrochloride salt of 4-(trifluoromethyl)-5-(2,6-dimorpholinopyrimidin-4-yl)pyridin-2-amine.

Embodiment 22. A combined preparation according to embodiment 21, wherein N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the active ingredient(s) in (ii) are the sole active ingredients.

Embodiment 23. A combined preparation according to any of embodiments 15 to 22 wherein the active ingredient 8-(6-amino-5-((2-(trifluoromethyl)pyridin-3-yl)thio) pyrazin-2-yl)-8-azaspiro[4.5]decan-1-amine is in the form of a racemate.

Embodiment 24. A combined preparation according to any of embodiments 15 to 22 wherein the active ingredient 8-(6-amino-5-((2-(trifluoromethyl)pyridin-3-yl)thio) pyrazin-2-yl)-8-azaspiro[4.5]decan-1-amine is in the (R) form.

Embodiment 25. A combined preparation according to any of embodiments 15 to 22 wherein the active ingredient 8-(6-amino-5-((2-(trifluoromethyl)pyridin-3-yl)thio) pyrazin-2-yl)-8-azaspiro[4.5]decan-1-amine is in the (S) form.

Embodiment 26. A pharmaceutical composition comprising a combination as defined in any one of embodiments 1 to 9 and at least one pharmaceutically acceptable carrier.

Embodiment 27. A pharmaceutical composition according to embodiment 26, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and the active ingredient(s) in (ii) in free form or in pharmaceutically acceptable salt form are provided in synergistically effective amounts for use in the treatment of a proliferative disease, such as cancer, in particular liver cancer.

Embodiment 28. A commercial package comprising a pharmaceutical combination as defined in any one of embodiments 1 to 9 together with instructions for simultaneous or sequential administration thereof for use in the delay of progression or treatment of a proliferative disease, such as cancer, in particular liver cancer.

Embodiment A:

Embodiment 1a: A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form.

Embodiment 2a: A pharmaceutical combination according to embodiment 1a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3a: A pharmaceutical combination according to embodiment 1a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and (ii) 3-(2,6-dichloro-3,5-dimethoxy-phenyl)-1-{6-[4-(4-ethyl-piperazin-1-yl)-phenylamino]-pyrimidin-4-yl}-1-methyl-urea is in citrate salt form.

Embodiment 4a: A pharmaceutical combination according to any of embodiments 1a to 3a, wherein 3-(2,6-dichloro-3,5-dimethoxy-phenyl)-1-{6-[4-(4-ethyl-piperazin-1-yl)-phenylamino]-pyrimidin-4-yl}-1-methyl-urea is in monophosphate salt form.

Embodiment 5a: A pharmaceutical combination according to any one of embodiments 1a to 4a further comprising at least one pharmaceutically acceptable carrier.

Embodiment 6a: A pharmaceutical combination according to any one of the preceding embodiments, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form are the sole active ingredients.

Embodiment 7a: A pharmaceutical combination according to any one of the preceding embodiments for use as a medicament.

Embodiment 8a: A pharmaceutical combination according any one of the preceding embodiments for use in the treatment of a proliferative disease, such as cancer, in particular liver cancer.

Embodiment 9a: Use of a pharmaceutical combination according to any one of embodiments 1a to 6a for the manufacture of a medicament for the treatment of a proliferative disease, such as cancer, in particular liver cancer.

Embodiment 10a: Use of a pharmaceutical combination according to any one of embodiments 1a to 6a for the manufacture of a pharmaceutical composition for the treatment of a proliferative disease, such as cancer, in particular liver cancer.

Embodiment 11a: A pharmaceutical combination according to any one of embodiments 1a to 6a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form are provided in synergistically effective amounts for use in the treatment of a proliferative disease, such as cancer, in particular liver cancer.

Embodiment 12a: A combined preparation comprising (1) one or more unit dosage forms of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and (2) one or more unit dosage forms of 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form.

Embodiment 13a: A combined preparation according to embodiment 12a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form, are the sole active ingredients.

Embodiment 14a: A combined preparation according to embodiment 12a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 15a: A combined preparation according to embodiment 14a, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form, are the sole active ingredients.

Embodiment 16a: A combined preparation according to embodiment 12a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 17a: A combined preparation according to embodiment 16a, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form are the sole active ingredients.

Embodiment 18a: A combined preparation according to any of embodiments 12a to 17a, wherein 3-(2,6-dichloro-3,5-dimethoxy-phenyl)-1-{6-[4-(4-ethyl-piperazin-1-yl)-phenylamino]-pyrimidin-4-yl}-1-methyl-urea is in monophosphate salt form.

Embodiment 19a: A combined preparation according to embodiment 18a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the monophosphate salt of 3-(2,6-dichloro-3,5-dimethoxy-phenyl)-1-{6-[4-(4-ethyl-piperazin-1-yl)-phenylamino]-pyrimidin-4-yl}-1-methyl-urea are the sole active ingredients.

Embodiment 20a: A pharmaceutical composition comprising a combination as defined in any one of embodiments 1a to 6a and at least one pharmaceutically acceptable carrier.

Embodiment 21a: A pharmaceutical composition according to embodiment 20a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form are provided in synergistically effective amounts for use in the treatment of a proliferative disease, such as cancer, in particular liver cancer.

Embodiment 22a: A commercial package comprising a pharmaceutical combination as defined in any one of embodiments 1a to 6a together with instructions for simultaneous or sequential administration thereof for use in the delay of progression or treatment of a proliferative disease, such as cancer, in particular liver cancer.

Embodiment B:

Embodiment 1b: A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) 8-(6-amino-5-((2-(trifluoromethyl)pyridin-3-yl)thio)pyrazin-2-yl)-8-azaspiro[4.5]decan-1-amine in free form or in pharmaceutically acceptable salt form.

Embodiment 2b: A pharmaceutical combination according to embodiment 1a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3b: A pharmaceutical combination according to embodiment 1a, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 4b: A pharmaceutical combination according to any of embodiments 1b to 3b, wherein 8-(6-amino-5-((2-(trifluoromethyl)pyridin-3-yl)thio)pyrazin-2-yl)-8-azaspiro[4.5]decan-1-amine is in free form.

Embodiment 5b: A pharmaceutical combination according to any of embodiments 1b to 4b, wherein 8-(6-amino-5-((2-(trifluoromethyl)pyridin-3-yl)thio)pyrazin-2-yl)-8-azaspiro[4.5]decan-1-amine is in the form of a racemate.

Embodiment 6b: A pharmaceutical combination according to any of embodiments 1b to 4b, wherein 8-(6-amino-5-((2-(trifluoromethyl)pyridin-3-yl)thio)pyrazin-2-yl)-8-azaspiro[4.5]decan-1-amine is in (R) form.

Embodiment 7b: A pharmaceutical combination according to any of embodiments 1b to 4b, wherein 8-(6-amino-5-((2-(trifluoromethyl)pyridin-3-yl)thio)pyrazin-2-yl)-8-azaspiro[4.5]decan-1-amine is in (S) form.

Embodiment 8b: A pharmaceutical combination according to any one of embodiments 1b to 7b further comprising at least one pharmaceutically acceptable carrier.

Embodiment 9b: A pharmaceutical combination according to any one of the preceding embodiments, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 8-(6-amino-5-((2-(trifluoromethyl)pyridin-3-yl)thio)pyrazin-2-yl)-8-azaspiro[4.5]decan-1-amine in free form or in pharmaceutically acceptable salt form are the sole active ingredients.

Embodiment 10b: A pharmaceutical combination according to any one of the preceding embodiments for use as a medicament.

Embodiment 11b: A pharmaceutical combination according any one of the preceding embodiments for use in the treatment of a proliferative disease, such as cancer, in particular liver cancer.

Embodiment 12b: Use of a pharmaceutical combination according to any one of embodiments 1b to 9b for the manufacture of a medicament for the treatment of a proliferative disease, such as cancer, in particular liver cancer.

Embodiment 13b: Use of a pharmaceutical combination according to any one of embodiments 1b to 9b for the manufacture of a pharmaceutical composition for the treatment of a proliferative disease, such as cancer, in particular liver cancer.

Embodiment 14b: A pharmaceutical combination according to any one of embodiments 1b to 9b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 8-(6-amino-5-((2-(trifluoromethyl)pyridin-3-yl)thio)pyrazin-2-yl)-8-azaspiro[4.5]decan-1-amine in free form or in pharmaceutically acceptable salt form are provided in synergistically effective amounts for use in the treatment of a proliferative disease, such as cancer, in particular liver cancer.

Embodiment 15b: A combined preparation comprising (1) one or more unit dosage forms of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and (2) one or more unit dosage forms of 8-(6-amino-5-((2-(trifluoromethyl)pyridin-3-yl)thio)pyrazin-2-yl)-8-azaspiro[4.5]decan-1-amine in free form or in pharmaceutically acceptable salt form in free form or in pharmaceutically acceptable salt form.

Embodiment 16b: A combined preparation according to embodiment 15b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 8-(6-amino-5-((2-(trifluoromethyl)pyridin-3-yl)thio)pyrazin-2-yl)-8-azaspiro[4.5]decan-1-amine in free form or in pharmaceutically acceptable salt form in free form or in pharmaceutically acceptable salt form, are the sole active ingredients.

Embodiment 17b: A combined preparation according to embodiment 15b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 18b: A combined preparation according to embodiment 17b, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and 8-(6-amino-5-((2-(trifluoromethyl)pyridin-3-yl)thio)pyrazin-2-yl)-8-azaspiro[4.5]decan-1-amine in free form or in pharmaceutically acceptable salt form, are the sole active ingredients.

Embodiment 19b: A combined preparation according to embodiment 15b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 20b: A combined preparation according to embodiment 19b, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and 8-(6-amino-5-((2-(trifluoromethyl)pyridin-3-yl)thio)pyrazin-2-yl)-8-azaspiro[4.5]decan-1-amine in free form or in pharmaceutically acceptable salt form are the sole active ingredients.

Embodiment 21b: A combined preparation according to any of embodiments 15b to 20b, wherein 8-(6-amino-5-((2-(trifluoromethyl)pyridin-3-yl)thio)pyrazin-2-yl)-8-azaspiro[4.5]decan-1-amine is in free form.

Embodiment 22b: A combined preparation according to any of embodiment 15b to 21b, wherein 8-(6-amino-5-((2-(trifluoromethyl)pyridin-3-yl)thio)pyrazin-2-yl)-8-azaspiro[4.5]decan-1-amine is in the form of a racemate.

Embodiment 23b: A combined preparation according to any of embodiments 15b to 21b, wherein 8-(6-amino-5-((2-(trifluoromethyl)pyridin-3-yl)thio)pyrazin-2-yl)-8-azaspiro[4.5]decan-1-amine is in the (R) form.

Embodiment 24b: A combined preparation according to any of embodiments 15b to 21b, wherein 8-(6-amino-5-((2-(trifluoromethyl)pyridin-3-yl)thio)pyrazin-2-yl)-8-azaspiro[4.5]decan-1-amine is in the (S) form.

Embodiment 25b: A combined preparation according to any of embodiment 21b to 24b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 8-(6-amino-5-((2-(trifluoromethyl)pyridin-3-yl)thio)pyrazin-2-yl)-8-azaspiro[4.5]decan-1-amine in free form are the sole active ingredients.

Embodiment 26b: A pharmaceutical composition comprising a combination as defined in any one of embodiments 1b to 9b and at least one pharmaceutically acceptable carrier.

Embodiment 27b: A pharmaceutical composition according to embodiment 26b, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 8-(6-amino-5-((2-(trifluoromethyl)pyridin-3-yl)thio)pyrazin-2-yl)-8-azaspiro[4.5]decan-1-amine in free form or in pharmaceutically acceptable salt form are provided in synergistically effective amounts for use in the treatment of a proliferative disease, such as cancer, in particular liver cancer.

Embodiment 28b: A commercial package comprising a pharmaceutical combination as defined in any one of embodiments 1b to 9b together with instructions for simultaneous or sequential administration thereof for use in the delay of progression or treatment of a proliferative disease, such as cancer, in particular liver cancer.

Embodiment D:

Embodiment 1d: A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and (ii) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form.

Embodiment 2d: A pharmaceutical combination according to embodiment 1d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3d: A pharmaceutical combination according to embodiment 1d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 4d: A pharmaceutical combination according to any of embodiments 1d to 3d, wherein 7-Cyclopentyl-2-(5-piperazin-1-yl-pyridin-2-ylamino)-7H-pyrrolo[2,3-d]pyrimidine-6-carboxylic acid dimethylamide is in succinate salt form.

Embodiment 5d: A pharmaceutical combination according to any one of embodiments 1d to 4d further comprising at least one pharmaceutically acceptable carrier.

Embodiment 6d: A pharmaceutical combination according to any one of the preceding embodiments, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form are the sole active ingredients.

Embodiment 7d: A pharmaceutical combination according to any one of the preceding embodiments for use as a medicament.

Embodiment 8d: A pharmaceutical combination according any one of the preceding embodiments for use in the treatment of a proliferative disease, such as cancer, in particular liver cancer.

Embodiment 9d: Use of a pharmaceutical combination according to any one of embodiments 1d to 6d for the manufacture of a medicament for the treatment of a proliferative disease, such as cancer, in particular liver cancer.

Embodiment 10d: Use of a pharmaceutical combination according to any one of embodiments 1 d to 6d for the manufacture of a pharmaceutical composition for the treatment of a proliferative disease, such as cancer, in particular liver cancer.

Embodiment 11d: A pharmaceutical combination according to any one of embodiments 1d to 6d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form, are provided in synergistically effective amounts for use in the treatment of a proliferative disease, such as cancer, in particular liver cancer.

Embodiment 12d: A combined preparation comprising (1) one or more unit dosage forms of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (2) one or more unit dosage forms of 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form.

Embodiment 13d: A combined preparation according to embodiment 12d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form are the sole active ingredients.

Embodiment 14d: A combined preparation according to embodiment 12d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 15d: A combined preparation according to embodiment 14d, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form are the sole active ingredients.

Embodiment 16d: A combined preparation according to embodiment 12d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 17d: A combined preparation according to embodiment 16d, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form are the sole active ingredients.

Embodiment 18d: A combined preparation according to any of embodiments 12d to 17d, wherein 7-Cyclopentyl-2-(5-piperazin-1-yl-pyridin-2-ylamino)-7H-pyrrolo[2,3-d]pyrimidine-6-carboxylic acid dimethylamide is in succinate salt form.

Embodiment 19d: A combined preparation according to embodiment 18d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the succinate salt of 7-Cyclopentyl-2-(5-piperazin-1-yl-pyridin-2-ylamino)-7H-pyrrolo[2,3-d]pyrimidine-6-carboxylic acid dimethylamide are the sole active ingredients.

Embodiment 20d: A pharmaceutical composition comprising a combination as defined in any one of embodiments 1d to 6d and at least one pharmaceutically acceptable carrier.

Embodiment 21d: A pharmaceutical composition according to embodiment 20d, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form are provided in synergistically effective amounts for use in the treatment of a proliferative disease, such as cancer, in particular liver cancer.

Embodiment 22d: A commercial package comprising a pharmaceutical combination as defined in any one of embodiments 1d to 6d together with instructions for simultaneous or sequential administration thereof for use in the delay of progression or treatment of a proliferative disease, such as cancer, in particular liver cancer.

Embodiment E:

Embodiment 1e: A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form.

Embodiment 2e: A pharmaceutical combination according to embodiment 1e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3e: A pharmaceutical combination according to embodiment 1e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 4e: A pharmaceutical combination according to any of embodiments 1e to 3e wherein (S)-N1-(4-methyl-5-(2-(1,1,1-trifluoro-2-methylpropan-2-yl)pyridin-4-yl)thiazol-2-yl)pyrrolidine-1,2-dicarboxamide is in free form.

Embodiment 5e: A pharmaceutical combination according to any one of embodiments 1e to 4e further comprising at least one pharmaceutically acceptable carrier.

Embodiment 6e: A pharmaceutical combination according to any one of the preceding embodiments, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form are the sole active ingredients.

Embodiment 7e: A pharmaceutical combination according to any one of the preceding embodiments for use as a medicament.

Embodiment 8e: A pharmaceutical combination according any one of the preceding embodiments for use in the treatment of a proliferative disease, such as cancer, in particular liver cancer.

Embodiment 9e: Use of a pharmaceutical combination according to any one of embodiments 1e to 6e for the manufacture of a medicament for the treatment of a proliferative disease, such as cancer, in particular liver cancer.

Embodiment 10e: Use of a pharmaceutical combination according to any one of embodiments 1e to 6e for the manufacture of a pharmaceutical composition for the treatment of a proliferative disease, such as cancer, in particular liver cancer.

Embodiment 11e: A pharmaceutical combination according to any one of embodiments 1e to 6e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form, are provided in synergistically effective amounts for use in the treatment of a proliferative disease, such as cancer, in particular liver cancer.

Embodiment 12e: A combined preparation comprising (1) one or more unit dosage forms of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (2) one or more unit dosage forms of (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form.

Embodiment 13e: A combined preparation according to embodiment 12e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form are the sole active ingredients.

Embodiment 14e: A combined preparation according to embodiment 12e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 15e: A combined preparation according to embodiment 14e, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form are the sole active ingredients.

Embodiment 16e: A combined preparation according to embodiment 12e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 17e: A combined preparation according to embodiment 16e, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form are the sole active ingredients.

Embodiment 18e: A combined preparation according to any of embodiments 12e to 17e, wherein (S)-N1-(4-methyl-5-(2-(1,1,1-trifluoro-2-methylpropan-2-yl)pyridin-4-yl)thiazol-2-yl)pyrrolidine-1,2-dicarboxamide is in free form.

Embodiment 19e: A combined preparation according to embodiment 18e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the free form of (S)-N1-(4-methyl-5-(2-(1,1,1-trifluoro-2-methylpropan-2-yl)pyridin-4-yl)thiazol-2-yl)pyrrolidine-1,2-dicarboxamide are the sole active ingredients.

Embodiment 20e: A pharmaceutical composition comprising a combination as defined in any one of embodiments 1e to 6e and at least one pharmaceutically acceptable carrier.

Embodiment 21e: A pharmaceutical composition according to embodiment 20e, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (S)-N1-(4-methyl-5-(2-(1,1,1-trifluoro-2-methylpropan-2-yl)pyridin-4-yl)thiazol-2-yl)pyrrolidine-1,2-dicarboxamide in free form or in pharmaceutically acceptable salt form, are provided in synergistically effective amounts for use in the treatment of a proliferative disease, such as cancer, in particular liver cancer.

Embodiment 22e: A commercial package comprising a pharmaceutical combination as defined in any one of embodiments 1e to 6e together with instructions for simultaneous or sequential administration thereof for use in the delay of progression or treatment of a proliferative disease, such as cancer, in particular liver cancer.

Embodiment F:

Embodiment 1f: A pharmaceutical combination comprising (i) N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and (ii) 4-(trifluoromethyl)-5-(2,6-dimorpholinopyrimidin-4-yl)pyridin-2-amine in free form or in pharmaceutically acceptable salt form.

Embodiment 2f: A pharmaceutical combination according to embodiment 1f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 3f: A pharmaceutical combination according to embodiment 1f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 4f: A pharmaceutical combination according to any of embodiments 1f to 3f, wherein 4-(trifluoromethyl)-5-(2,6-dimorpholinopyrimidin-4-yl)pyridin-2-amine is in the hydrochloride salt form.

Embodiment 5f: A pharmaceutical combination according to any one of embodiments 1f to 4f further comprising at least one pharmaceutically acceptable carrier.

Embodiment 6f: A pharmaceutical combination according to any one of the preceding embodiments, wherein N-(5-cyano-4-((2-methoxyethyl)amino)pyridin-2-yl)-7-formyl-6-

((4-methyl-2-oxopiperazin-1-yl)methyl)-3,4-dihydro-1,8-naphthyridine-1(2H)-carboxamide in free form or in pharmaceutically acceptable salt form, and 4-(trifluoromethyl)-5-(2,6-dimorpholinopyrimidin-4-yl)pyridin-2-amine in free form or in pharmaceutically acceptable salt form are the sole active ingredients.

Embodiment 7f: A pharmaceutical combination according to any one of the preceding embodiments for use as a medicament.

Embodiment 8f: A pharmaceutical combination according any one of the preceding embodiments for use in the treatment of a proliferative disease, such as cancer, in particular liver cancer.

Embodiment 9f: Use of a pharmaceutical combination according to any one of embodiments 1f to 6f for the manufacture of a medicament for the treatment of a proliferative disease, such as cancer, in particular liver cancer.

Embodiment 10f: Use of a pharmaceutical combination according to any one of embodiments 1f to 6f for the manufacture of a pharmaceutical composition for the treatment of a proliferative disease, such as cancer, in particular liver cancer.

Embodiment 11f: A pharmaceutical combination according to any one of embodiments 1f to 6f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 4-(trifluoromethyl)-5-(2,6-dimorpholinopyrimidin-4-yl)pyridin-2-amine in free form or in pharmaceutically acceptable salt form, are provided in synergistically effective amounts for use in the treatment of a proliferative disease, such as cancer, in particular liver cancer.

Embodiment 12f: A combined preparation comprising (1) one or more unit dosage forms of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and (2) one or more unit dosage forms of 4-(trifluoromethyl)-5-(2,6-dimorpholinopyrimidin-4-yl)pyridin-2-amine in free form or in pharmaceutically acceptable salt form.

Embodiment 13f: A combined preparation according to embodiment 12f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form, and 4-(trifluoromethyl)-5-(2,6-dimorpholinopyrimidin-4-yl)pyridin-2-amine in free form or in pharmaceutically acceptable salt form, are the sole active ingredients.

Embodiment 14f: A combined preparation according to embodiment 12f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in free form.

Embodiment 15f: A combined preparation according to embodiment 14f, wherein the free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, and 4-(trifluoromethyl)-5-(2,6-dimorpholinopyrimidin-4-yl)pyridin-2-amine in free form or in pharmaceutically acceptable salt form, are the sole active ingredients.

Embodiment 16f: A combined preparation according to embodiment 12f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is in citrate salt form.

Embodiment 17f: A combined preparation according to embodiment 16f, wherein the citrate salt of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide and 4-(trifluoromethyl)-5-(2,6-dimorpholinopyrimidin-4-yl)pyridin-2-amine in free form or in pharmaceutically acceptable salt form are the sole active ingredients.

Embodiment 18f: A combined preparation according to any of embodiments 12f to 17f, wherein 4-(trifluoromethyl)-5-(2,6-dimorpholinopyrimidin-4-yl)pyridin-2-amine is in hydrochloride salt form.

Embodiment 19f: A combined preparation according to embodiment 18f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and the hydrochloride salt of 4-(trifluoromethyl)-5-(2,6-dimorpholinopyrimidin-4-yl)pyridin-2-amine are the sole active ingredients.

Embodiment 20f: A pharmaceutical composition comprising a combination as defined in any one of embodiments 1f to 6f and at least one pharmaceutically acceptable carrier.

Embodiment 21f: A pharmaceutical composition according to embodiment 20f, wherein N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form or in pharmaceutically acceptable salt form and 4-(trifluoromethyl)-5-(2,6-dimorpholinopyrimidin-4-yl)pyridin-2-amine in free form or in pharmaceutically acceptable salt form, are provided in synergistically effective amounts for use in the treatment of a proliferative disease, such as cancer, in particular liver cancer.

Embodiment 22f: A commercial package comprising a pharmaceutical combination as defined in any one of embodiments 1f to 6f together with instructions for simultaneous or sequential administration thereof for use in the delay of progression or treatment of a proliferative disease, such as cancer, in particular liver cancer.

The following Examples illustrate the invention described above; they are not, however, intended to limit the scope of the invention in any way. The beneficial effects of the pharmaceutical combination of the present invention can also be determined by other test models known as such to the person skilled in the pertinent art.

| Abbreviation | Description |
| --- | --- |
| aq. | aqueous |
| conc. | concentrated |
| DAST | (diethylamino)sulfur trifluoride |
| dba | dibenzylideneacetone |
| DCC | Dicyclohexylcarbodiimide |
| DCM | dichloromethane |
| DIPEA | N,N-diisopropylethylamine, N-ethyl-N-isopropylpropan-2-amine |
| DMA | N,N-dimethylacetamide |
| DMAP | 4-dimethylaminopyridine |
| DME | 1,2-dimethoxyethane |
| DMF | N,N-dimethylformamide |
| DMSO | dimethylsulfoxide |
| DMSO-$d_6$ | Hexadeuterodimethyl sulfoxide |
| dppf | 1,1'-bis(diphenylphosphino)ferrocene |
| DSC | Differential scanning calorimetry |
| ESI-MS | Electrospray ionization mass spectroscopy |
| h | hour |
| HPLC | High-performance liquid chromatography |

-continued

| Abbreviation | Description |
|---|---|
| KHMDS | Potassium hexamethyldisilazide |
| l/ml | liter/milliliter |
| LC-MS | liquid chromatography and mass spectrometry |
| LHMDS | Lithium hexamethyldisilazide |
| M | molar |
| min | minutes |
| mp | Melting point |
| MW | microwave |
| mw | Molecular weight |
| m/z | mass to charge ratio |
| NBS | N-bromosuccinimide |
| NCS | N-chlorosuccinimide |
| NIS | N-iodosuccinimide |
| NMP | N-methylpyrrolidinone, 1-methyl-2-pyrrolidinone |
| NMR | Nuclear magnetic resonance |
| org. | organic |
| RP | Reverse phase |
| sat | saturated |
| SFC | Supercritical fluid chromatography |
| TBAF | tetrabutylammonium fluoride |
| TFA | trifluoroacetic acid |
| THF | tetrahydrofurane |
| $t_R$ or Rt or RT | Retention time (if not indicated, in minutes) |
| UPLC | Ultra-performance liquid chromatography |

Other Abbreviations
HUH7=human hepatoma cell line 7
HCC=hepatocellular carcinoma
ATCC=American Type Culture Collection
CTG=CellTiter Glo
CI=Combination index
ATP=Adenosine Triphosphate
PBS=Phosphate Buffered Saline
$Et_2O$=diethyl ether
EtOAc=ethyl acetate
DIEA or DIPEA=N,N-diisopropyl-ethylamine
HPLC=High Performance Liquid Chromatography
mL=milliliter(s)
$Pd_2(dba)_3$=tris(dibenzylideneacetone)dipalladium
Xantophos=4,5-bis(diphenylphosphino)-9,9-dimethylxanthene (Xantophos)

The following abbreviations are used in the Experimental section to refer to compounds:
CPi=N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide,
CPii-a=3-(2,6-dichloro-3,5-dimethoxy-phenyl)-1-{6-[4-(4-ethyl-piperazin-1-yl)-phenylamino]-pyrimidin-4-yl}-1-methyl-urea monophosphate salt;
CPii-b=(R)-8-(6-amino-5-((2-(trifluoromethyl)pyridin-3-yl)thio)pyrazin-2-yl)-8-azaspiro[4.5]decan-1-amine
CPii-d=7-Cyclopentyl-2-(5-piperazin-1-yl-pyridin-2-ylamino)-7H-pyrrolo[2,3-d]pyrimidine-6-carboxylic acid dimethylamide succinate salt
CPii-e=(S)-N1-(4-methyl-5-(2-(1,1,1-trifluoro-2-methyl-propan-2-yl)pyridin-4-yl)thiazol-2-yl)pyrrolidine-1,2-dicarboxamide
CPii-f=4-(trifluoromethyl)-5-(2,6-dimorpholinopyrimidin-4-yl)pyridin-2-amine hydrochloride salt

EXAMPLES

The synthesis of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated herein as CPi and also named as Example 83) and salts thereof is disclosed in PCT/IB2014/065585, the content of which are incorporated by reference, as described herein below:

Example 83

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide

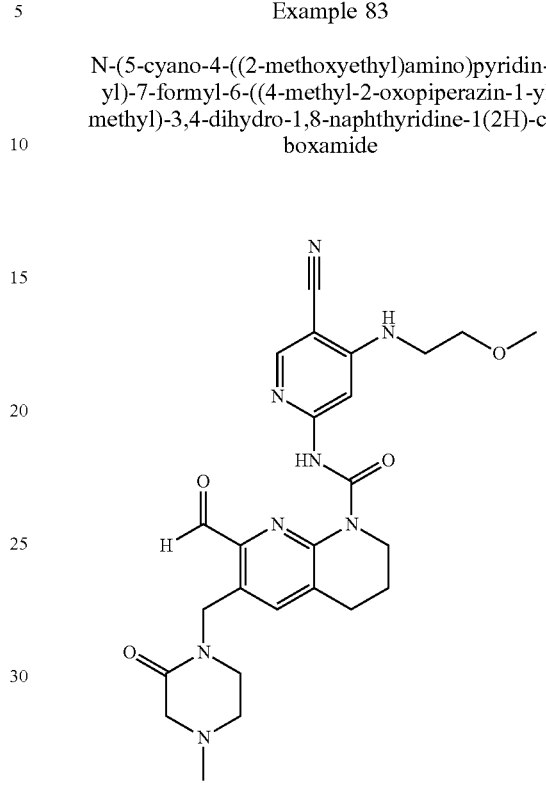

Concentrated hydrochloric acid (0.40 ml) was added to a solution of N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide (intermediate 80, 470 mg, 0.808 mmol) in THF (3 ml) and water (1 ml) at room temperature. After stirring for 3 h at room temperature saturated aqueous $NaHCO_3$ was added, the mixture extracted with DCM (3×), the organic layers dried over $Na_2SO_4$ and evaporated. The residue was sonicated with EtOAc (6 ml) and pentane (6 ml) and then filtered. The white solid obtained was then dissolved in DCM (6 ml), EtOAc added (3 ml), the solution warmed, sealed and allowed to stand at room temperature for 2 h. Filtration and drying gave the title compound as a white solid.

$^1$H NMR (400 MHz, DMSO-$d_6$) δ 13.43 (s, 1H), 10.06 (s, 1H), 8.24 (s, 1H), 7.49 (s, 1H), 7.47 (s, 1H), 6.96 (t, br, 1H), 4.86 (s, 2H), 3.96-3.90 (m, 2H), 3.52-3.46 (m, 2H), 3.39-3.33 (m, 2H), 3.30-3.21 (m, 2H), 3.37 (s, 3H), 3.02 (s, 2H), 2.93-2.86 (m, 2H), 2.61-2.56 (m, 2H), 2.21 (s, 3H), 1.95-1.85 (m, 2H).

(UPLC-MS 6) $t_R$ 0.70, ESI-MS 507.2, [M+H]$^+$.

The following salts were prepared from the above free form of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide by precipitation with the appropriate counterions.

Malate with 1:1 stoichiometry (mw 640.66), mp (DSC) 181.1° C. (onset): Acetone (2 ml) was added to a mixture of malic acid (26.4 mg, 0.197 mmol) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg, 0.197 mmol) and the mixture heated on a mini-block with heating-cooling cycles from 55 to 5° C. for 7 repeat cycles (heating rate: 1.5° C./min, cooling rate: 0.25° C./min). The white solid was collected by centrifugation and dried for 18 h at 40° C. to give the title salt.

Tartrate with 1:0.5 stoichiometry (mw 581.72), mp (DSC) 176.7° C. (onset). A solution of tartaric acid (75.7 mg) in methanol (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with methanol (2 ml), and dried for 18 h at 40° C. under vacuum to give the title salt.

Tartrate with 1:1 stoichiometry (mw 656.66), mp (DSC) 169.9° C. (onset): A solution of tartaric acid (75.7 mg) in acetone (5 ml) was prepared at room temperature (0.1 M). A portion of the 0.1 M tartaric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:0.5 stoichiometry (mw 602.73), mp (DSC) 168.4° C. (onset): A solution of citric acid (96.9 mg) in methanol (5 ml) was prepared at room temperature (0.1 M). A portion of the 0.1 M citric acid in methanol solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in methanol (4 ml) and the mixture sonicated for 1 minute then heated at 55° C. with stirring for 2 h. The white solid was then collected by filtration, washing 2× with acetone (2 ml), and dried for 18 h at 40° C. under vacuum to give the title salt.

Citrate with 1:1 stoichiometry (mw 698.70), mp (DSC) 168.8° C. (onset): A solution of citric acid (96.9 mg) in acetone (5 ml) was prepared at room temperature (0.1 M). A portion of the 0.1 M citric acid in acetone solution (2 ml) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in acetone (4 ml) and the mixture sonicated for 1 minute then heated at 55° C. with stirring for 2 h before slowly cooling to room temperature. The white solid was then collected by filtration, washing 2× with acetone (2 ml), and dried for 18 h at 40° C. under vacuum to give the title salt.

Alternatively, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (6.5 g, 12.83 mmol) was placed in a 500 ml 4-flask reactor. 49 ml of glacial acetic acid was added and the resulting suspension was stirred at 23° C. until a clear mixture was obtained. In a separate flask, anhydrous 2-hydroxypropane-1,2,3-tricarboxylic acid (2.59 g, 13.47 mmol, 1.05 equiv.) was dissolved in 49 ml of glacial acetic acid at 50° C. until a clear solution was obtained. This solution was then added at 23° C. to the N-(5-cyano-4-((2-methoxyethyl)amino)pyridin-2-yl)-7-formyl-6-((4-methyl-2-oxopiperazin-1-yl) methyl)-3,4-dihydro-1,8-naphthyridine-1(2H)-carboxamide solution previously prepared. This mixture was stirred for 30 min at 23° C. and then added dropwise over 1 h to 192 ml of ethyl acetate warmed to 75° C. The temperature remained constant over the addition. At the end of the addition, the temperature of the mixture was cooled slowly to 23° C. and let 16 h at this temperature under gentle stirring. The suspension was cooled to 5-10° C. and filtered. The cake was washed with 15 ml of ethyl acetate and 15 ml of acetone. The wet cake (ca 8.5 g) was transferred in a 500 ml flask containing 192 ml of dry acetone. The resulting suspension was refluxed for 24 h. The suspension was filtered and the cake was washed with 2 times 15 ml of dry acetone then dried at 50° C. under vacuum for several hours to give the title salt.

Intermediate 80

N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide A solution of 6-amino-4-((2-methoxyethyl)amino)nicotinonitrile (intermediate 75, 481 mg, 2.50 mmol) in anhydrous DMF (1.5 ml) was added drop wise over 10 minutes to a mixture of di(1H-1,2,4-triazol-1-yl)methanone (410 mg, 2.50 mmol) and DMF (1.5 ml) cooled at 0° C. After stirring for 45 minutes at 0° C. the reaction mixture was allowed to warm to room temperature and after a further 90 minutes at room temperature a solution of 1-((2-(dimethoxymethyl)-5,6,7,8-tetrahydro-1,8-naphthyridin-3-yl)methyl)-4-methyl-piperazin-2-one (intermediate 81, 418 mg, 1.00 mmol) in DMF (2 ml) was added. The reaction mixture was stirred for 17.5 h at room temperature, quenched by the addition of MeOH and evaporated. The residue was applied to a 80 g RediSep® silica column as a DCM solution and purified by normal phase chromatography, eluting with a gradient from DCM to 2% MeOH in DCM. Product containing fractions were combined and evaporated to give the title compound as an orange foam. $^1$H NMR (400 MHz, DMSO-d$_6$) δ 13.50 (s, 1H), 8.27 (s, 1H), 7.52 (s, 1H), 7.39 (s, 1H), 6.93 (t, 1H), 5.45 (s, 1H), 4.65 (s, 2H), 3.94-3.89 (m, 2H), 3.54-3.50 (m, 2H), 3.40-3.35 (m, 2H), 3.38 (s, 6H), 3.29 (s, 3H), 3.20-3.16 (m, 2H), 3.05 (s, 2H), 2.86-2.80 (m, 2H), 2.61-2.55 (m, 2H), 2.22 (s, 3H), 1.94-1.88 (m, 2H). (UPLC-MS 6) $t_R$ 0.72; ESI-MS 553.3 [M+H]$^+$.

Intermediate 81

1-((2-(dimethoxymethyl)-5,6,7,8-tetrahydro-1,8-naphthyridin-3-yl)methyl)-4-methylpiperazin-2-one Sodium triacetoxyborohydride (3.10 g, 14.61 mmol) was added to a mixture of 2-(dimethoxymethyl)-5,6,7,8-tetrahydro-1,8-naphthyridine-3-carbaldehyde (intermediate 41, 2.30 g, 9.74 mmol), ethyl 2-((2-aminoethyl)(methyl)amino) acetate dihydrochloride (intermediate 82, 2.6 g, 14.61 mmol) and triethylamine (6.75 ml, 48.7 mmol) in 1,2-dichloroethane (20 ml) at room temperature. The reaction mixture was stirred for 21 h at room temperature and additional sodium triacetoxyborohydride (2.6 g, 9.74 mmol) was added. After a further 4 h stirring at room temperature, again additional sodium triacetoxyborohydride (1.3 g, 4.87 mmol) was added and the reaction maintained at 4° C. for 2.5 days. The reaction mixture was then warmed to room temperature, saturated aqueous NaHCO$_3$ solution added, the mixture extracted with DCM (3×), the combined organic layers dried over Na$_2$SO$_4$ and evaporated. The residue was applied to a 120 g RediSep® silica column as a DCM solution and purified by normal phase chromatography, eluting with a gradient from DCM to 10% MeOH in DCM. Product containing fractions were combined and evaporated to give the title compound as an orange foam. $^1$H NMR (400 MHz, CDCl$_3$) δ 7.08 (s, 1H), 5.30 (s, br, 1H), 5.20 (s, 1H), 4.69 (s, 2H), 3.44-3.34 (m, 2H), 3.40 (s, 6H), 3.22-3.15 (m, 2H), 3.24 (s, 2H), 2.71-2.64 (m, 2H), 2.58-2.50 (m, 2H), 2.31 (s, 3H), 1.98-1.82 (m, 2H). (UPLC-MS 6) t$_R$ 0.33; ESI-MS 335.3 [M+H]$^+$.

Intermediate 82

Ethyl 2-((2-aminoethyl)(methyl)amino)acetate dihydrochloride

Concentrated hydrochloric acid (10 ml) was added to a solution of ethyl 2-((2-((tert-butoxycarbonyl)amino)ethyl)(methyl)amino)acetate (intermediate 83, 3.05 g, 11.13 mmol) in THF (20 ml) and EtOH (100 ml) at room temperature. After stirring 1 h at room temperature the reaction mixture was evaporated, ethanol (20 ml) added, evaporated, further ethanol (50 ml) added and then stirred at 60° C. for 70 min. The cooled reaction mixture was then evaporated to give the title compound as a pale-yellow glass. $^1$H NMR (400 MHz, DMSO-d$_6$) δ 8.58 (s, br, 3H), 4.19 (q, 2H), 4.26-4.15 (m, 2H), 3.44 (s, br, 2H), 3.21 (s, br, 2H), 2.88 (s, 3H), 1.21 (t, 3H).

Intermediate 83

Ethyl 2-((2-((tert-butoxycarbonyl)amino)ethyl) (methyl)amino)acetate

Ethyl bromoacetate (1.27 ml, 11.48 mmol) was added to a mixture of tert-butyl (2-(methylamino)ethyl)carbamate (2.0 g, 11.48 mmol), triethylamine (4.81 ml) and THF (24 ml) at 0° C. After stirring 24 h at room temperature the reaction mixture was partitioned between saturated aqueous NaHCO$_3$ and DCM, extracted 2× with DCM, the organic layers dried over Na$_2$SO$_4$ and evaporated to give the title compound as a clear pale-yellow oil. $^1$H NMR (400 MHz, CDCl$_3$) δ 5.20 (s, br, 1H), 4.18 (q, 2H), 3.24 (s, 2H), 3.22-3.16 (m, 2H), 2.65-2.61 (m, 2H), 2.38 (s, 3H), 1.42 (s, 9H), 1.24 (t, 3H).

Intermediate 41

2-(dimethoxymethyl)-5,6,7,8-tetrahydro-1,8-naphthyridine-3-carbaldehyde

To a solution of 6-bromo-7-(dimethoxymethyl)-1,2,3,4-tetrahydro-1,8-naphthyridine (intermediate 12, 15.0 g, 52.2 mmol) in THF (400 ml) at −78° C. under argon, was added MeLi (1.6 M in Et$_2$O, 32.6 ml, 52.2 mmol), the solution was stirred for 5 min, then n-BuLi (1.6 M in hexane, 35.9 ml, 57.5 mmol) was added slowly and the solution was stirred for 20 min. THF (100 ml) was added to the reaction at −78° C. Subsequently, n-BuLi (1.6 M in hexane, 49.0 ml, 78 mmol) was added and the reaction mixture was stirred for 20 min, then again n-BuLi (1.6 M in hexane, 6.53 ml, 10.45 mmol) was added and the mixture was stirred for 10 min at −78° C. DMF (2.10 ml, 27.2 mmol) was added and the reaction mixture was stirred at −78° C. for 45 min, then it was allowed to warm to room temperature, poured into sat. aq. NH$_4$Cl and extracted twice with DCM. The combined organic phases were dried over Na$_2$SO$_4$, filtered and evaporated to give the title compound as an orange oil. (UPLC-MS 3) t$_R$ 0.63 min; ESI-MS 237.2 [M+H]$^+$.

Intermediate 12

6-bromo-7-(dimethoxymethyl)-1,2,3,4-tetrahydro-1,8-naphthyridine

Into a 3 l 4-necked round-bottom flask was placed 7-(dimethoxymethyl)-1,2,3,4-tetrahydro-1,8-naphthyridine (intermediate 4, 114.6 g, 550.3 mmol) in acetonitrile (2 l). This was followed by the addition of NBS (103 g, 578 mol) in portions with stirring at 25° C. The resulting solution was stirred for 30 min at 25° C. The resulting mixture was concentrated under vacuum and the residue was diluted with 1000 ml of diethylether. The mixture was washed with 3×100 ml of ice/water. The aqueous phase was extracted with 2×100 ml of diethylether and the organic layers were combined. The resulting mixture was washed with 1×100 ml of brine, dried over sodium sulfate and concentrated under vacuum to give the title compound as a light yellow solid. LC-MS: (ES, m/z): 286.03 [M+H]$^+$. $^1$H-NMR: (300 MHz, CDCl$_3$) δ 1.86-1.94 (2H, m), 2.70-2.74 (2H, m), 3.9-3.43 (2H, m), 3.47 (6H, s), 5.23 (1H, s), 5.58 (1H, s), 7.29 (1H, s).

Intermediate 4

7-(dimethoxymethyl)-1,2,3,4-tetrahydro-1,8-naphthyridine

The procedure described in *J. Org. Chem.*, 2004, 69 (6), pp 1959-1966 was used. Into a 5-l pressure tank reactor (5 atm) was placed 2-(dimethoxymethyl)-1,8-naphthyridine (intermediate 5, 200 g, 979 mmol), ethanol (3 l), PtO$_2$ (12 g). The reactor was evacuated and flushed three times with nitrogen, followed by flushing with hydrogen. The mixture was stirred overnight at 23° C. under an atmosphere of hydrogen. This reaction was repeated four times. The solids were filtered out and the resulting mixture was concentrated under vacuum to give the title compound as a yellow solid.

Intermediate 5

2-(dimethoxymethyl)-1,8-naphthyridine

The procedure described in *J. Org. Chem.*, 2004, 69 (6), pp 1959-1966 was used. Into a 20 l 4-necked round-bottom flask was placed 2-aminopyridine-3-carbaldehyde (1000 g, 8.19 mol), 1,1-dimethoxypropan-2-one (1257 g, 10.64 mol), ethanol (10 l), and water (2 l). This was followed by the addition of a solution of sodium hydroxide (409.8 g, 10.24 mol) in water (1000 ml) drop wise with stirring at 0-15° C. The solution was stirred for 3 h at 0-20° C. and then concentrated under vacuum. The resulting solution was extracted with 3×1200 ml of ethyl acetate and the organic layers were combined. The mixture was dried over sodium sulfate and concentrated under vacuum. The residue was washed with 3×300 ml of hexane and the solid was collected by filtration. This resulted in the title compound as a yellow solid. $^1$H-NMR (400 MHz, DMSO-d$_6$) δ 9.11 (dd, 1H), 8.53 (d, 1H), 8.50 (dd, 1H), 7.73 (d, 1H), 7.67 (dd, 1H), 5.44 (s, 1H), 3.41 (s, 6H).

Intermediate 75

6-amino-4-((2-methoxyethyl)amino)nicotinonitrile

A solution of 6-amino-4-fluoronicotinonitrile (intermediate 21, 1.10 g, 8.02 mmol) in DMA (20 ml) was treated with 2-methoxyethylamine (2.07 ml, 24.1 mmol) and DIPEA (4.20 mL, 24.1 mmol), heated to 50° C. and stirred for 15 h. The reaction mixture was cooled to room temperature and concentrated. The crude material was purified by normal phase chromatography (24 g silica gel cartridge, heptanes/EtOAc 100:0 to 0:100). The product containing fractions were concentrated and dried under vacuum to give the title compound as an off-white solid.

An alternative synthesis of 6-amino-4-((2-methoxyethyl)amino)nicotinonitrile is outlined below:

To tert-butyl N-{5-cyano-4-[(2-methoxyethyl)amino]pyridin-2-yl}carbamate (intermediate 287, 7 g) was added 30-36% aqueous HCl (40 ml), the mixture stirred at room temperature for 30 minutes and monitored by chromatography until complete conversion. The solution was then basified with 20-30% NaOH solution to pH=9-10 and filtered to give a white solid. The solid was added to ethyl acetate (15 ml) and heated to 50-55° C. to form a clear solution. The solution was then cooled to 3-6° C., stirred for 2-3 h and filtered. The wet cake was then dried to give the title compound as a white solid. $^1$H NMR (400 MHz, DMSO-d$_6$) δ 7.92 (s, 1H), 6.39 (s, 2H), 6.15 (t, 1H), 5.61 (s, 1H), 3.46 (t, 2H), 3.27 (s, 3H), 3.24 (q, 2H). (UPLC-MS 3) t$_R$ 0.62; ESI-MS 193.1 [M+H]$^+$.

$^1$H-NMR (400 MHz, DMSO-d$_6$) δ 7.14 (d, 1H), 6.51 (d, 1H), 6.47-6.41 (m, 1H), 4.98 (s, 1H), 3.28-3.19 (m, 2H), 3.23 (s, 6H), 2.64 (t, 2H), 1.73-1.79 (m, 2H).

Intermediate 21

6-amino-4-fluoronicotinonitrile 4-fluoro-5-iodopyridin-2-amine (intermediate 22, 240 g, 1 mol), zinc cyanide (125 g, 1.05 mol), zinc (13 g, 0.2 mol), Pd$_2$(dba)$_3$ (25 g, 25 mmol) and dppf (55 g, 0.1 mol) in DMA (800 ml) were degassed and charged into the round bottom flask under nitrogen. The mixture was stirred at 100° C. for 3 h. The reaction mixture was diluted with 5% NaHCO$_3$ (2 l), extracted with EtOAc (4×600 ml). The combined organic layers were washed with 5% NaOH (1 l), dried over Na$_2$SO$_4$, concentrated to 700 ml. The resulting organic phase was eluted through silica gel column with EtOAc (1.7 l). The combined organic filtrate was washed with 2 M HCl (3×800 ml). The pH of the aqueous phase was adjusted to 10 with saturated NaHCO$_3$. The aqueous phase was extracted whit DCM (3×500 ml). The combined DCM was dried over Na$_2$SO$_4$ and concentrated. The residue was further purified by column chromatography (eluted with pentane: EtOAc 10:1 to 3:2) followed by recrystallization from pentane/EtOAc 3/1 to give the title compound as white solid. $^1$H NMR (400 MHz, DMSO-d$_6$) δ 8.40 (d, 1H), 7.40 (s, 2H), 6.34 (d, 1H).

Intermediate 22

4-fluoro-5-iodopyridin-2-amine

A suspension of 4-fluoropyridin-2-amine (336 g, 2.5 mol) and NIS (745 g, 2.75 mol) in MeCN (9 l) was treated with TFA (114 g, 1 mol). The reaction mixture was then stirred at room temperature for 8 h. The reaction mixture was diluted with EtOAc (10 l), washed with sat. aq. Na$_2$S$_2$O$_3$ (2×5 l), brine (4×5 l). The combined organic layers were dried over Na$_2$SO$_4$, filtered and concentrated to get the crude product. The crude product was purified by recrystallization from EtOAc/pentane (1/10) to afford the title compound as a white solid. $^1$H NMR (400 MHz, DMSO-d$_6$) δ 8.14 (d, 1H), 6.45 (s, 2H), 6.33 (d, 1H).

Intermediate 287

Tert-butyl (5-cyano-4-((2-methoxyethyl)amino)pyridin-2-yl)carbamate

A mixture of tert-butyl (4-chloro-5-cyanopyridin-2-yl) carbamate (intermediate 288, 9.8 g, 38.6 mmol), 2-methoxyethylamine (5.8 g, 77.3 mmol) and DIPEA (6 g, 46.4 mmol) in DMSO (80 ml) was heated at 65-70° C. for 24 h and monitored by chromatography until complete conversion. The solution was then cooled to room temperature and a white solid precipitated gradually. Water (20 ml) was then added slowly within 1 h. The suspension was stirred for a further 1 h, filtered and dried to give the title compound as a white solid. $^1$H NMR (DMSO-d$_6$, 400 MHz): δ 9.87 (s, 1H), 8.18 (s, 1H), 7.20 (s, 1H), 6.86 (s, 9H), 3.51 (t, 2H), 3.36 (t, 2H), 3.28 (s, 3H), 1.47 (s, 9H).

Intermediate 288

Tert-butyl (4-chloro-5-cyanopyridin-2-yl)carbamate

A mixture of 2,4-dichloro-5-cyanopyridine (10 g, 57.8 mmol), tert-butyl carbamate (8.2 g, 70.5 mmol), Pd(OAc)$_2$ (0.26 g, 1.1 mmol), Xantphos (1.34 g, 2.3 mmol) and K$_2$CO$_3$ (12 g, 87 mmol) in THF (150 ml) was degassed 3× with nitrogen. The mixture was then heated at 70° C. for 4-5 h and monitored by chromatography until complete conversion. Following completion of the reaction, additional THF (100 ml) was added and heated the mixture at 70° C. for additional 1 h and then cooled to room temperature. The suspension was then filtered through a pad of celite to remove the solid. The filtrate was then concentrated and azotropically distilled with ethyl acetete before filtering to give the title compound. $^1$H NMR (DMSO-d$_6$, 400 MHz): δ 10.82 (s, 1H), 8.79 (s, 1H), 8.09 (s, 1H), 1.49 (s, 9H).

In-Vitro Biochemical Kinase Assays for Example 83:

Assays were performed in 384 well microtiter plates. Each assay plate contained 8-point serial dilutions for the test compound, as well as four 8-point serial dilutions of staurosporine as reference compound, plus 16 high and 16 low controls.

Liquid handling and incubation steps were done on an Innovadyne Nanodrop Express equipped with a robotic arm (Thermo CatX, Caliper Twister II) and an incubator (Liconic STX40, Thermo Cytomat 2C450). The assay plates were prepared by addition of 50 nl per well of compound solution in 90% DMSO. The kinase reactions were started by stepwise addition of 4.5 μl per well of peptide/ATP-solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 16 mM MgCl2, 1122 μM ATP, 4 μM peptide (5-Fluo-Ahx-KKKKEEIYFFFG-NH2, Biosyntan GmbH) and 4.5 μl per well of enzyme solution (50 mM HEPES, pH 7.5, 1 mM DTT, 0.02% Tween20, 0.02% BSA, 0.6% DMSO, 10 mM beta-glycerophosphate, and 10 μM sodium orthovanadate, 16 mM MgCl2, 6 nM FGFR4 (GST-FGFR4(388-802), produced in-house by expression in insect cells and affinity chromatography). Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compound was dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. The dilution protocol included the production of "pre-dilution plates", "master plates" and "assay plates".

Pre-dilution plates: 96 polypropylene well plates were used as pre-dilution plates. A total of 4 pre-dilution plates were prepared including test compound each on the plate positions A1-A10, one standard compound at A11 and one DMSO control at A12. All dilution steps were done on a HamiltonSTAR robot.

Master plates: 30 µL of the individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 µM, respectively in 90% of DMSO.

Assay plates: Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

In Vitro Cellular Kinase Assays for FGFR4

As a read out for cellular FGFR4 kinase activity, an assay that measures the Tyrosine phosphorylation content on FGFR4 was developed. For this, a BaF3-Tel-FGFR4 cell line was generated: BaF3 cells were stably transduced with a retrovirus encoding a fusion protein consisting of the amino terminal portion of TEL (aa1-337) fused to the cytoplasmic domain of FGFR4, including the yuxtamembrane domain. The presence of the TEL domain mediates constitutive activation of the fused FGFR4 kinase by oligomerization, and thus autophosphorylation on the Tyrosine sites.

A MSD (Meso Scale Discovery)-based capture ELISA was developed and used as follows:

Cell treatment: 250000 BaF3-Tel-FGFR4 cells per well were seeded in 96-well tissue culture plates (Corning Cat#3359) in 40 uL of growth medium (RPMI-1640 (Amimed Cat#1-41F01-I) supplemented with 10% foetal calf serum, 10 mM HEPES, 1 mM Sodium Pyruvate, 2 mM Stable Glutamine and 1× Penicillin-Streptomycin). Using a liquid handling device (Velocity 11 Bravo, Agilent), serial 3-fold dilutions of the compounds were prepared in DMSO, prediluted in growth medium, followed by transfer of 10 uL/well to the cell plates. After incubation for 1 hour at 37° C./5% CO2, 50 uL of lysis buffer (150 mM NaCl, 20 mM Tris (pH 7.5), 1 mM EDTA, 1 mM EGTA, 1% Triton X-100, 10 mM NaF, complemented with protease inhibitors (Complete Mini, Roche Cat#11836153001) and phosphatase) inhibitors (Phosphatase Inhib I, SIGMA Cat# P2850; Phosphatase Inhib II, SIGMA Cat# P5726 according to supplier instructions) was added and incubated for 30 minutes on ice with shaking at 300 rpm. Sample plates were then frozen and stored at 70° C. Following thawing on ice, the sample plates were centrifuged for 15 minutes at 1200 rpm at 6° C.

ELISA assay: Multi array 96 well plates (MSD, Cat# L15XB-3) were coated for 1 hour at room temperature with 25 uL/well of mouse anti-H-TEL antibody (Santa Cruz, Cat#sc-166835) diluted 1:400 in PBS/O. Following addition of 150 uL of 3% MSD-blocker A (Cat# R93BA-1) in TBS-T (50 mM Tris, 150 mM NaCl, 0.02% Tweeen-20), plates were incubated for 1 hour at room temperature with shaking. Plates were then washed 3 times with 200 uL/well of TBS-T. 50 uL of the cell lysate was then transferred to the coated plate and incubated for 15 hours at 4° C., followed by 3 washes with 200 µl TBS-T/well and addition of 25 µl/well of MSD SULFOTAGGED PY20 antibody (MSD Cat# R32AP-5), diluted 1:250 in TBS-T+1% MSD Blocker A. Following Incubation for 1 h at room temperature with shaking, wells were washed 3 times with 200 µl TBS-T/well. Following ition of 150 µl MSD Read Buffer (MSD, Cat# R92TC-2) stock solution diluted 1:4 with nano water, electro-chemiluminescent signal generation was immediately quantified on a SectorImager 6000 (MSD). IC50 calculation: For data analysis, the assay background was determined in wells containing medium and lysis buffer, but no cells, and the corresponding value subtracted from all data points. The effect of a particular test compound concentration on FGFR4 phosphorylation is expressed as percentage of the background-corrected electro-chemiluminescence reading obtained for cells treated with vehicle only (DMSO, 0.2% f.c.), which is set as 100. Compound concentrations leading to half-maximal signal inhibition (IC50) were determined by standard four parametric curve fitting (XLfit 5.4, IDBS).

Cell Proliferation Assay

Methylene blue staining proliferation assay (MBS): The effect of the compound on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-I), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Specifically, 5000 cells/well were seeded in 96-well tissue culture plates (TPP Cat#92696) in a total media volume of 100 µl/well and increasing compound dilutions or DMSO were added 24 hours thereafter in triplicates. 72 hours after compound addition, cells were fixed by adding 25 µL/well of 20% glutaraldehyde (Sigma Aldrich Cat# G400-4) and incubated for 10 minutes at room temperature. Cells were washed three times with H$_2$O, 200 µL/well and stained with 100 µL/well 0.05% methylene blue (ABCR GmbH Cat# AB117904) for 10 minutes at room temperature. Cells were washed 3 times with H$_2$O, 200 µL/well and then lysed by adding 200 µL/well of 3% HCl (Fluka Cat#84422) for 30 minutes at room temperature with shaking. Optical density was measured at A650 nm. The concentration of compound providing 50% of proliferation inhibition with respect to DMSO-treated cells was determined (IC$_{50}$) using XLFit software.

CellTiter Glo (CTG) assay: The functional effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-I), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Compound-mediated suppression of cell proliferation/viability is assessed by quantification of cellular ATP levels using the CellTiter-Glo (CTG) reagent (Promega, Cat# G7573). Briefly, cells are seeded at 3'000 cells/well/80 µl fresh medium into tissue-culture-treated 96-well plates (Costar Cat#3904), followed by addition of 20 µl medium containing compound dilutions at 5-fold their final intended concentration. Dose-response effects are assessed by 3-fold serial dilutions of the test compound, starting at 10 µM. Following incubation of the cells for 3 days at 37° C. and 5% CO2, the effect of inhibitors on cell viability is quantified following addition of 50 µl CTG and luminescence measurement (integration time: 500 ms) as per vendor manual, using a correspondingly equipped multi-mode plate reader (M200Pro, TECAN, Switzerland). For data analysis, the assay background value determined in wells containing medium, but no cells, is subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% f.c.), which is set as 100%, whereas the luminescence reading for wells containing medium only, but no cells, is set as −100%. Compound concentrations leading to half-maximal growth inhibition (GI50) are determined using standard four parameter curve fitting (XLfit 5.2., IDBS, UK).

| Example | Biochemical FGFR4 IC$_{50}$ (nM) | Cellular BaF$_3$ FGFR4 IC$_{50}$ (nM) | HUH7 proliferation (nM) | |
|---|---|---|---|---|
| | | | MBS | CTG |
| 83 | 1.9 | 4.3 | 12 | 60.9 |

Example 1

The synthesis of (S) and (R) 8-(6-amino-5-((2-(trifluoromethyl)pyridin-3-yl)thio)pyrazin-2-yl)-8-azaspiro[4.5]decan-1-amine is disclosed in PCT/IB2015/050345 as described herein below:

(S) and (R) 8-(6-amino-5-((2-(trifluoromethyl)pyridin-3-yl)thio)pyrazin-2-yl)-8-azaspiro[4.5]decan-1-amine

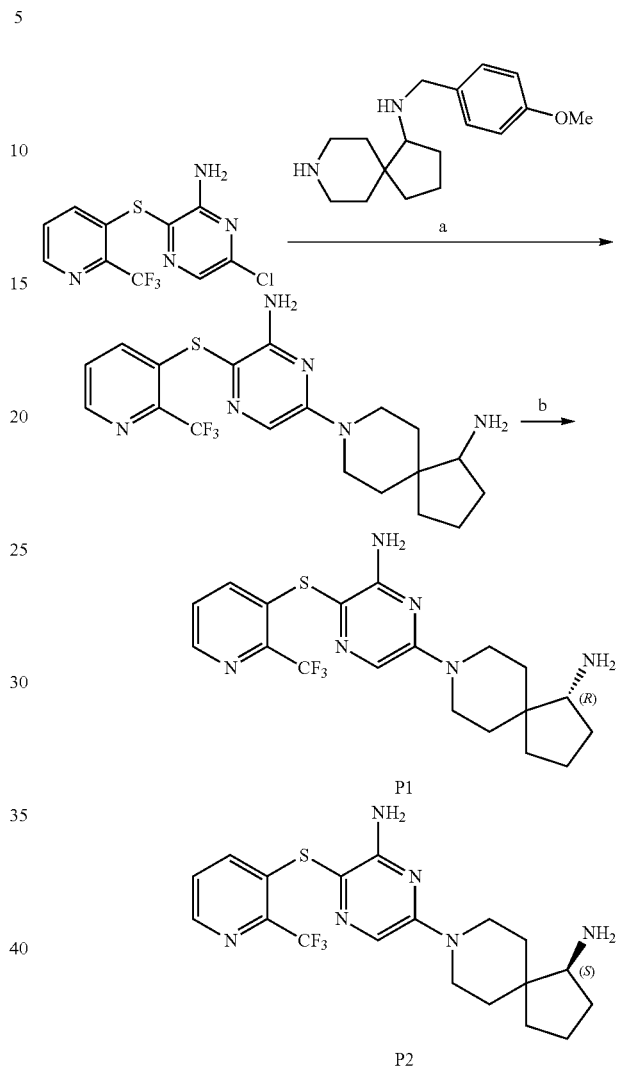

Step a: A solution of 6-chloro-3-((2-(trifluoromethyl)pyridin-3-yl)thio)pyrazin-2-amine (200 mg, 0.652 mmol) and N-(4-methoxybenzyl)-8-azaspiro[4.5]decan-1-amine (358 mg, 1.304 mmol) in DIPEA (3 mL) was stirred for 60 h at 130° C. After cooling to RT, the volatiles were removed under reduced pressure. The resulting residue was dissolved in TFA (3 mL) and the solution was stirred in a microwave reactor for 1 h at 160° C. and for 15 min at 180° C. The volatiles were removed under reduced pressure and the resulting residue was purified by HPLC (gradient elution 25-50% acetonitrile in water, 5 mM NH$_4$OH modifier) to give 8-(6-amino-5-((2-(trifluoromethyl)pyridin-3-yl)thio) pyrazin-2-yl)-8-azaspiro[4.5]decan-1-amine (73 mg, 0.482 mmol; 83% pure based on HRMS). 19 mg of this compound were further purified by HPLC (gradient elution 25-50% acetonitrile in water, 0.1% TFA modifier) to give the title compound pure (9.5 mg). $^1$H NMR (400 MHz, methanol-d$_4$) δ ppm 8.29 (dd, J=4.42, 1.39 Hz, 1 H), 7.48 (s, 1 H), 7.19-7.41 (m, 2 H), 4.06-4.26 (m, 2H), 2.89-3.14 (m, 2 H), 2.71 (t, J=7.33 Hz, 1 H), 1.86-2.00 (m, 1 H), 1.73-1.84 (m, 1 H), 1.43-1.72 (m, 5 H), 1.27-1.42 (m, 2 H), 1.17-1.27 (m, 1 H). $^{19}$F NMR (376 MHz, methanol-d$_4$) δ ppm −66.45 (s). HRMS calculated for C$_{19}$H$_{24}$N$_6$F$_3$S (M+H)$^+$ 425.1735, found 425.1753. IC$_{50}$ is 0.023 uM.

Step b: Chiral SFC purification of the above title compound performed as follows; column: ID 21×250 mm, flow rate: 75 g per minute, mobile phase: 35% MeOH and 10 mM NH$_4$OH in CO$_2$, detection: 270 nm UV to obtain single enantiomer R$_t$ (P1)=4.9 min; IC$_{50}$ is 0.011 uM and R$_t$ (P2)=6.4 min; IC$_{50}$ is 0.167 uM, wherein the IC50 refers to the ability to selectively inhibit SHP2 activity. The inhibitory properties were evidenced by testing in any one of the following assays:

SHP2 Allosteric Inhibition Assay

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat#3575) using a final reaction volume of 25 uL and the following assay buffer conditions: 60 mM HEPES, pH 7.2, 75 mM NaCl, 75 mM KCl, 1 mM EDTA, 0.05% P-20, 5 mM DTT.

The inhibition of SHP2 (concentrations varying from 0.003-100 μM) was monitored using an assay in which 0.5 nM of SHP2 was incubated with of 0.5 uM of peptide IRS1_pY1172(dPEG8)pY1222 (sequence: H2N-LN(pY)IDLDLV(dPEG8)LST(pY)ASINFQK-amide). After 30-60 minutes incubation at 25° C., the surrogate substrate DiF-MUP (Invitrogen, cat# D6567) was added to the reaction and incubated at 25° C. for 30 minutes. The reaction was then quenched by the addition of 5 ul of a 160 uM solution of bpV(Phen) (Enzo Life Sciences cat# ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized IC$_{50}$ regression curve fitting with control based normalization.

p-ERK Cellular Assay p-ERK cellular assay using the AlphaScreen® SureFire™ Phospho-ERK 1/2 Kit (PerkinElmer): KYSE-520 cells (30,000 cells/well) were grown in 96-well plate culture overnight and treated with Shp2 inhibitors at concentrations of 20, 6.6, 2.2, 0.74, 0.24, 0.08, 0.027 uM for 2 hrs at 37° C. Incubations were terminated by addition of 30 μL of lysis buffer (PerkinElmer) supplied with the SureFire phospho-extracellular signal-regulated kinase (pERK) assay kit (PerkinElmer). Samples were processed according to the manufacturers directions. The fluorescence signal from pERK was measured in duplicate using a 2101 multilabel reader (Perkin Elmer Envision). The percentage of inhibition was normalized by the total ERK signal and compared with the DMSO vehicle control.

Colony Formation Assay and Cell Proliferation Assay

KYSE-520 Cells (1500 cells/well) were plated onto 24-well plates in 300 uL medium (RPMI-1640 containing 10% FBS, Lonza). For drug treatment, compounds of the invention at various concentrations (20, 10, 5, 2.5, 1.25 uM) were added 24 hours and 5 days after cell plating. At day 11, colonies were stained with 0.2% crystal violet (MP Bio-medicals) and subsequently dissolved in 20% acetic acid for quantitation using a Spectramax reader (Thermo Scientific). In cell proliferation assay, cells (1500-cells/well) were plated onto 96-well plates in 100 uL medium (RPMI-1640 containing 10% FBS, Lonza). At day 6, 50 μL Celltiter-Glo reagent (Promega) was added, and the luminescent signal was determined according to the supplier's instruction (Promega).

Intermediate 1

6-chloro-3-((2-(trifluoromethyl)pyridin-3-yl)thio)pyrazin-2-amine

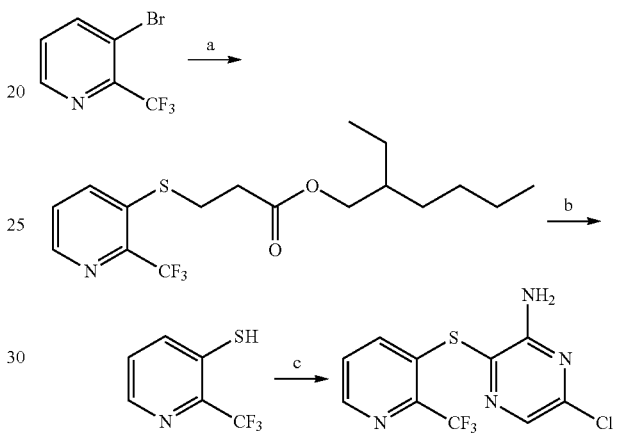

Step a: To a solution of 3-bromo-2-(trifluoromethyl)pyridine (1.0 g, 4.42 mmol), XantPhos (256 mg, 0.442 mmol), Pd$_2$(dba)$_3$ (203 mg, 0.221 mmol) in dioxane (12 mL) was added (at RT and under N$_2$) 2-ethylhexyl-3-mercaptopropanoate (1.1 mL, 4.87 mmol) followed by addition of DIPEA (1.55 mL, 8.85 mmol). The resulting solution was stirred in a microwave reactor for 1 h at 110° C. After cooling to RT, the reaction was filtered through a pad of Celite followed by EtOAc (25 mL) wash. The combined filtrates were concentrated and the resulting residue was purified by silica chromatography (0 to 30% gradient of EtOAc/heptane) to give 2-ethylhexyl 3-((2-(trifluoromethyl)pyridin-3-yl)thio)propanoate (1.41 g, 3.88 mmol). MS m/z 364.0 (M+H)$^+$.

Step b: To a solution of 2-ethylhexyl 3-((2-(trifluoromethyl)pyridin-3-yl)thio)propanoate (1.0 g, 2.75 mmol) in THF (8 mL) was added at −78° C. and under N$_2$ potassium tert-butoxide (1 M in THF, 8.25 mL, 8.25 mmol). After stirring vigorously at −78° C. for 20 min, the reaction was quenched with K$_2$CO$_3$ aq (2 M, 500 uL) and the volatiles were removed under reduced pressure. The resulting residue was poured into a separation funnel containing K$_2$CO$_3$ aq (2 M, 30 mL) and it was extracted with Et$_2$O (2×20 mL). The aqueous phase was acidified with 6 M HCl until pH 4 and the resulting cloudy suspension was extracted with CHCl$_3$: IPA (9:1; 3×20 mL) to give 2-(trifluoromethyl)pyridine-3-thiol (380 mg, 2.12 mmol). MS m/z 180.0 (M+H)$^+$.

Step c: To a solution of 2-(trifluoromethyl)pyridine-3-thiol (285 mg, 1.591 mmol), 3-bromo-6-chloropyrazin-2-amine (414 mg, 1.988 mmol), XantPhos (101 mg, 0.175 mmol), and Pd$_2$(dba)$_3$ (72.8 mg, 0.08 mmol) in dioxane (2 mL) was added (at RT and under N$_2$) DIPEA (556 uL, 3.18 mmol). The resulting solution was stirred in a microwave reactor for 1.5 h at 130° C. After cooling to RT, the reaction was diluted with EtOAc and it was filtered through a pad of Celite followed by EtOAc (25 mL) wash. The combined filtrates were concentrated and the resulting residue was purified by silica chromatography (0 to 30% gradient of EtOAc/heptane) to give 6-chloro-3-((2-(trifluoromethyl)pyridin-3-yl)thio)pyrazin-2-amine (1.41 g, 3.88 mmol). $^1$H NMR (400 MHz, CHLOROFORM-d) δ ppm 8.64 (dd, J=4.55, 1.26 Hz, 1 H), 7.90 (s, 1 H), 7.82 (dd, J=8.08, 0.76 Hz, 1 H), 7.46 (dd, J=8.08, 4.80 Hz, 1 H); $^{19}$F NMR (376 MHz, CHLOROFORM-d) δ ppm −64.34 (s, 1 F). MS m/z 307.1 (M+H)$^+$.

Intermediate 7

N-(4-methoxybenzyl)-8-azaspiro[4.5]decan-1-amine

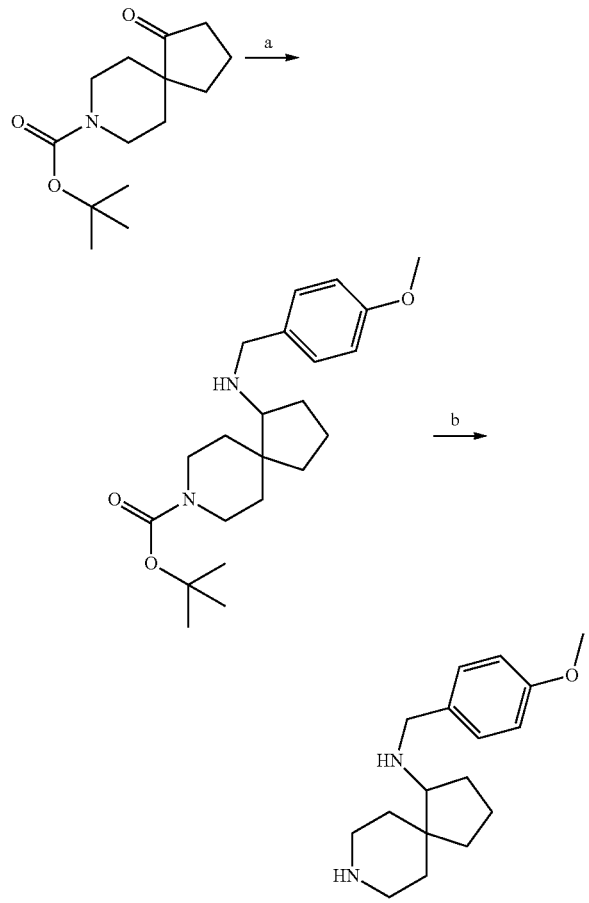

Step a: To a solution of tert-butyl 1-oxo-8-azaspiro[4.5]decane-8-carboxylate (1.8 g, 7.11 mmol), and (4-methoxyphenyl)methanamine (1.07 g, 7.82 mmol) in DCE (7 mL) was added sodium cyanoborohydride (2.23 g, 35.5 mmol) in portions and stirred at RT for 65 h. The mixture was diluted with saturated aqueous sodium bicarbonate solution (10 mL) and extracted with EtOAc (3×20 mL). The combined organic phases were washed with brine and concentrated. The resulting residue was purified by silica chromatography (0 to 2% gradient of MeOH/DCM, 0.25% Et$_3$N modified, followed by 0 to 50% gradient of EtOAc/heptane) to give tert-butyl 1-((4-methoxybenzyl)amino)-8-azaspiro[4.5]decane-8-carboxylate (1.1 g, 2.94 mmol) as a colorless wax. MS m/z 375.3 (M+H)$^+$.

Step b: A solution of tert-butyl 1-((4-methoxybenzyl)amino)-8-azaspiro[4.5]decane-8-carboxylate (1.1 g, 2.94 mmol) and TFA (2 mL) in DCM (2 mL) was stirred for 15 min at 0° C. The volatiles were removed under reduced pressure. The resulting residue was diluted with aqueous NaHCO$_3$ (10 mL) and extracted with EtOAc (4×10 mL) to give N-(4-methoxybenzyl)-8-azaspiro[4.5]decan-1-amine (0.8 g, 2.92 mmol) as a colorless oil. MS m/z 275.2 (M+H)$^+$.

Example 2

Cell Growth Inhibition and Synergy Assessment of the Hepatocellular Carcinoma Cell Line HUH7 after Treatment with Combinations of the Present Invention Cell proliferation assay: The human hepatocellular carcinoma cell line, HUH7, was purchased from American Type Culture Collection (ATCC). The cells were cultured in RPMI-1640 growth medium (ATCC, catalog number 20-2001), supplemented with 10% fetal bovine serum (GIBCO, catalog number F4135) at 37° C. in a humidified 5% CO$_2$ incubator. For the seven day cell proliferation assay, HUH7 cells were seeded at a density of 1500 cells per well in a tissue culture treated 96-well plate (Corning, catalog number 3904) and allowed to attach overnight at 37° C. in a humidified 5% CO$_2$ incubator. For the seven day dose matrix combination studies, the cells were exposed to serial dilutions of the following pairs of agents, either as single agents or in combination, in a checkerboard format: CPi+CPii-a, CPi+CPii-b, CPi+CPiid, or CPi+CPii-e. After seven days of treatment, cell growth was analyzed by measuring ATP levels using the CellTiter Glo (CTG) assay (Promega, catalog number G7572) as recommended by the manufacturer's instructions.

For the three day matrix combination studies, HUH7 cells were seeded at a density of 500 cells per well in tissue culture treated 384-well plates (Costar catalog number 3707) and allowed to attach overnight at 37° C. in a humidified 5% CO$_2$ incubator. The cells were then exposed to serial dilutions of CPi and CPii-f, either as single agents or in combination, using a checkerboard format. After three days of treatment, cell growth was analyzed by measuring ATP levels as described above, except that CTG was pre-diluted 1:1 in water prior to addition to the wells. Combination activity was determined according to the Loewe additivity model, using a custom-built software (Combination Analysis Module). Briefly, for each combination of two compounds in the concentration matrix, the combination effect is calculated as the difference between the measured inhibition and the inhibition according to the Loewe additivity model. Combination index (CI) is derived by the following equation:

$$CI = \frac{C(A)}{EC_{50}(A)} + \frac{C(B)}{EC_{50}(B)}$$

Where:
C(A) and C(B) are the concentrations of drug A and B that in combination cause 50% inhibition; and
EC50(A) and EC50(B) are the concentrations of drug A and B that individually cause 50% inhibition.
The CI Value quantitatively defines synergism (CI<1), additive effect (CI=1) and antagonism (CI>1).
Flow Cytometry was used to assess combination activity between CPi and CPii-e. The HUH7 cells were seeded in duplicate wells at a density of 1500 cells per well in a tissue culture treated 96-well plate (Corning, catalog number 3904) and allowed to attach overnight at 37° C. in a humidified 5% $CO_2$ incubator. The cells were then exposed to the following drug treatments: concentration range of CPi, concentration range of CPii-e and a combination of the two agents in a full concentration range matrix. After seven days of treatment, cells were washed twice with PBS, and then trypsinized cells were transferred to a low attach round bottom 96-well plate in a final volume of 200 ul. Cells were labeled with 10 uM final concentration of Sytox solution (LifeTechnologies catalog number S7020) according to the manufacturer's instructions. Analysis was completed using FloJo software. Combination activity was calculated as described above.

Figure 1B:
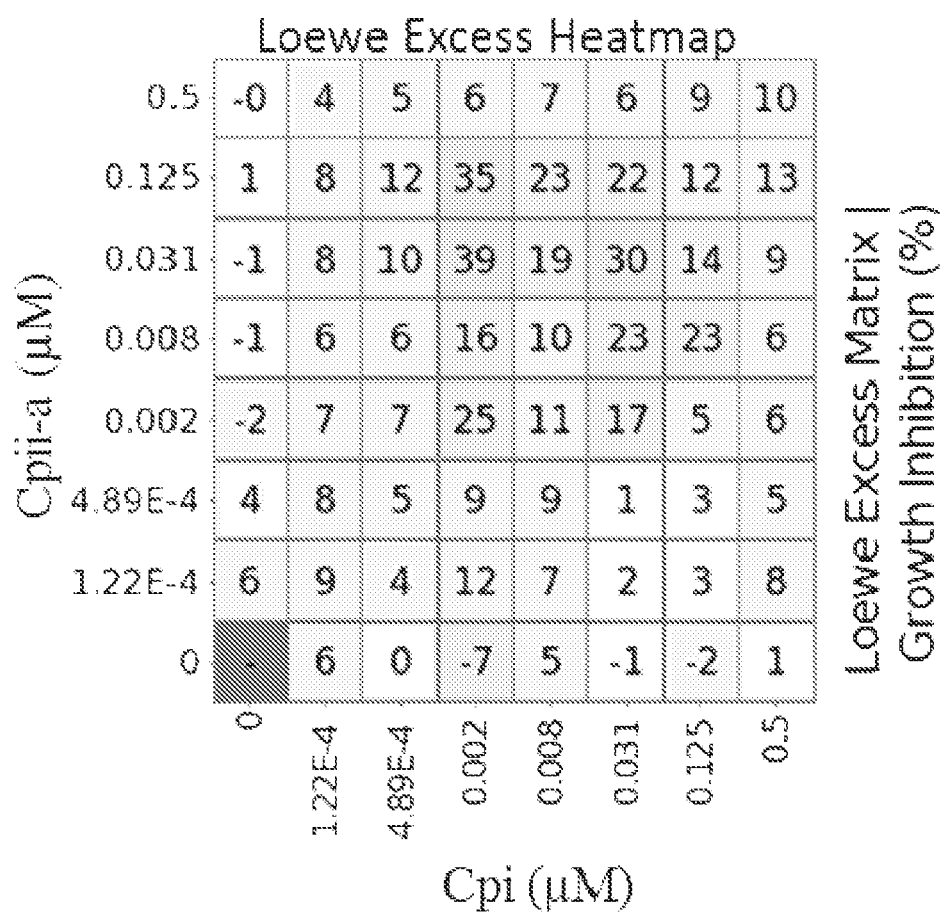
Figure 1C:
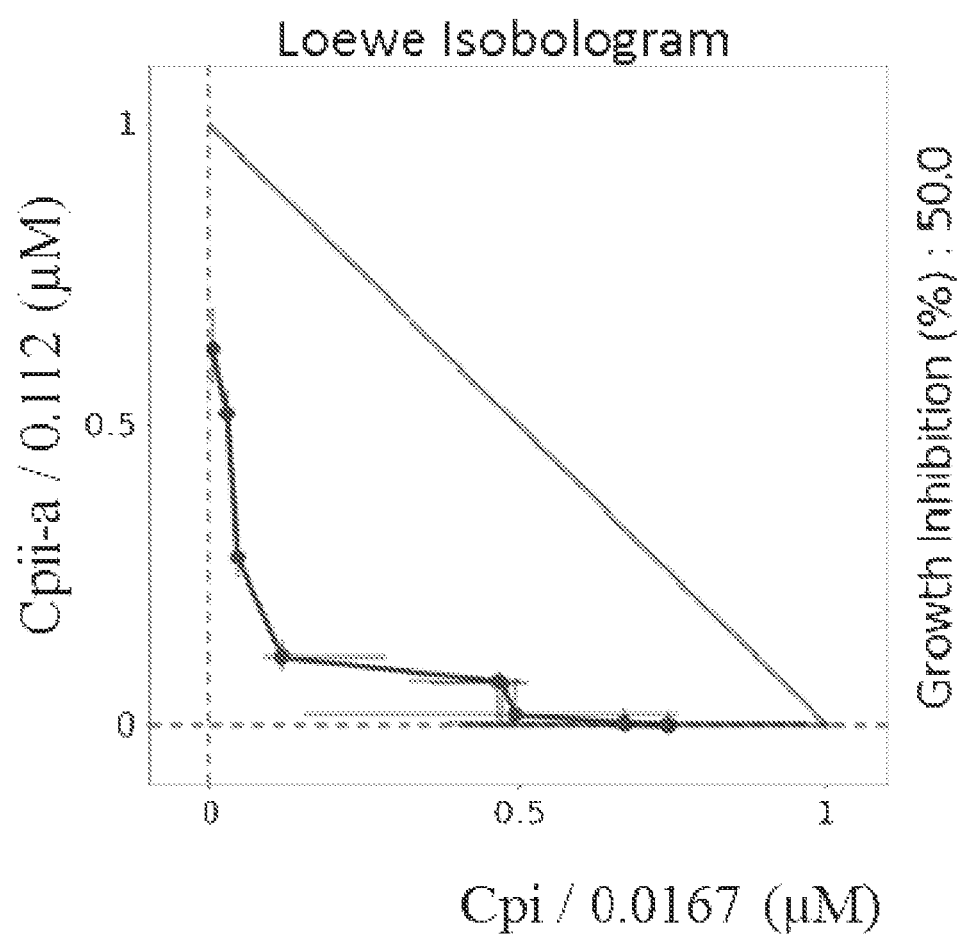

Results:

FIG. 1 illustrates the growth inhibition of HUH7 cells when treated with a concentration range of 3-(2,6-dichloro-3,5-dimethoxy-phenyl)-1-{6-[4-(4-ethyl-piperazin-1-yl)-phenylamino]-pyrimidin-4-yl}-1-methyl-urea monophosphate salt (abbreviated here as CPii-a) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated here as CPi) after seven days of treatment. Percent growth inhibition (Combination Data Heatmap) and synergy assessment for checkerboard combination of the two agents across a broad concentration matrix (Loewe Excess Heatmap) or the 50% growth inhibition level (Loewe Isobologram) are shown. Synergistic combination activity is observed in a full concentration matrix with CPi and CPii-a after seven days of treatment with a combination index of 0.327.

Figure 2A:
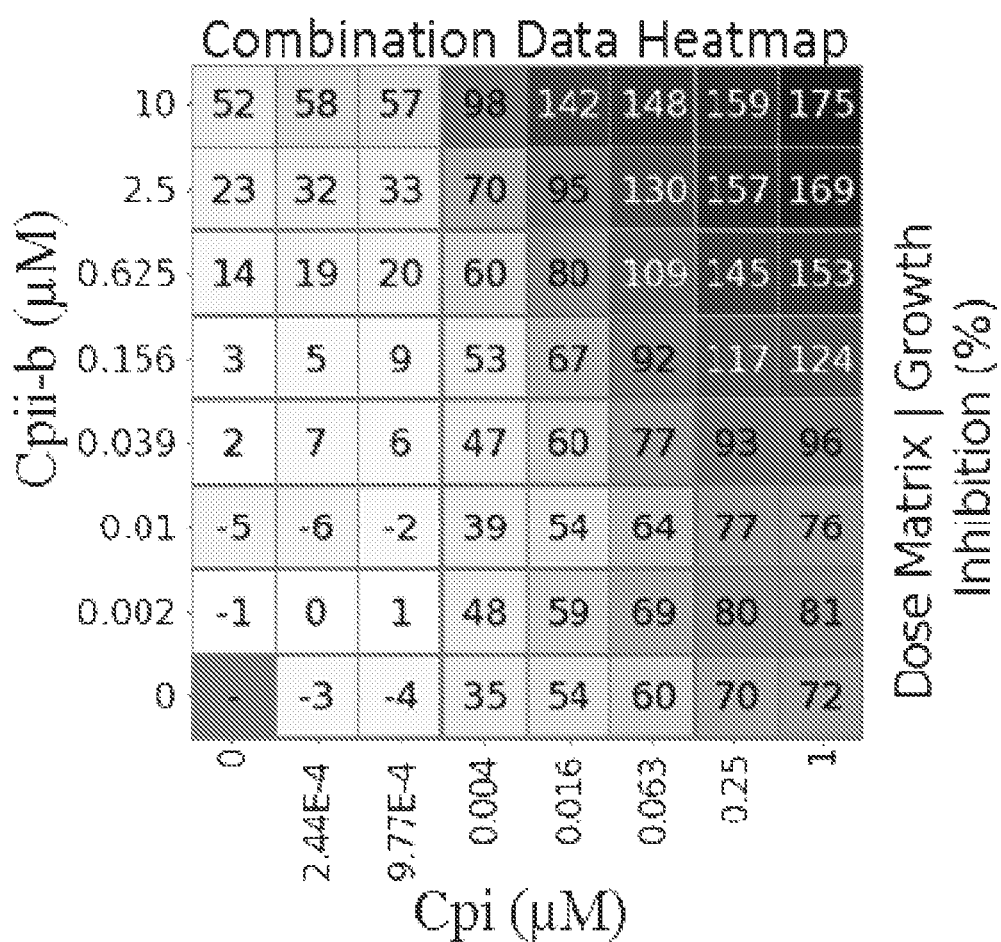
FIG. 2. Growth inhibition of HUH7 cells when treated with a concentration range of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated as CPi) and (R)-8-(6-amino-5-((2-(trifluoromethyl)pyridin-3-yl)thio)pyrazin-2-yl)-8-azaspiro[4.5]decan-1-amine (abbreviated as CPii-b) after seven days of treatment.
Figure 2B:
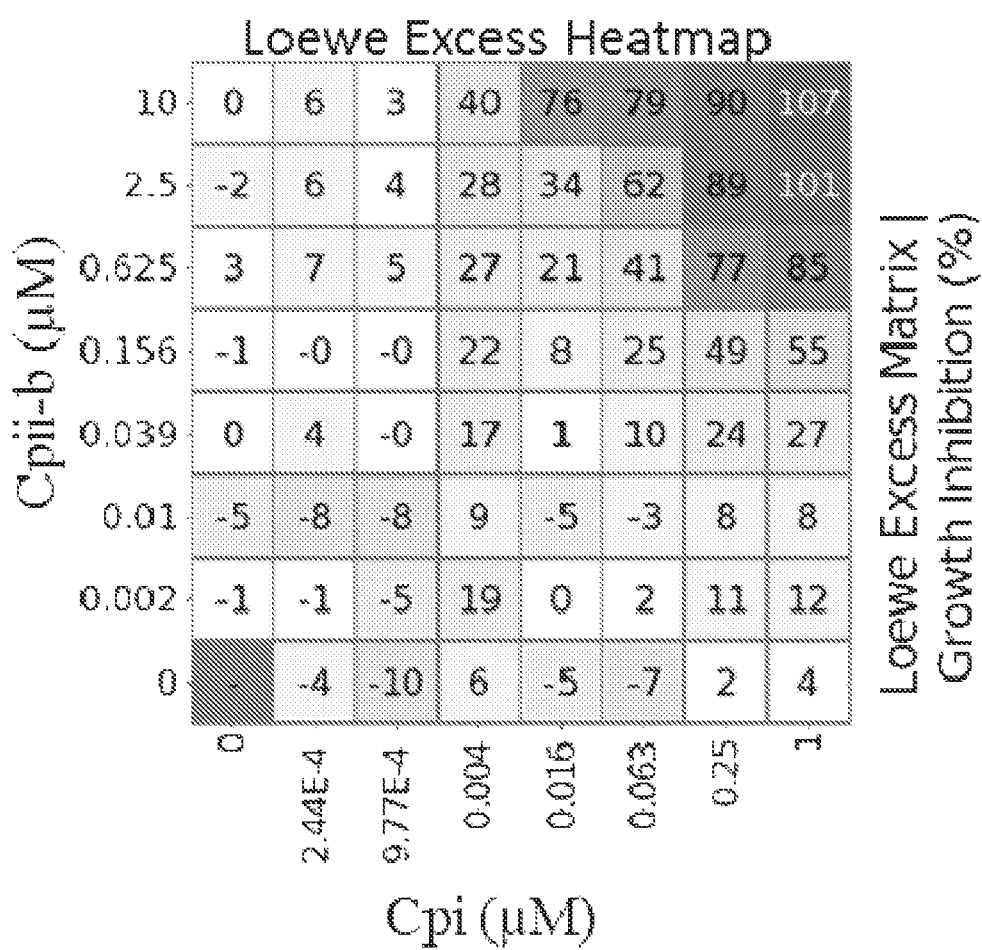
Figure 2C:
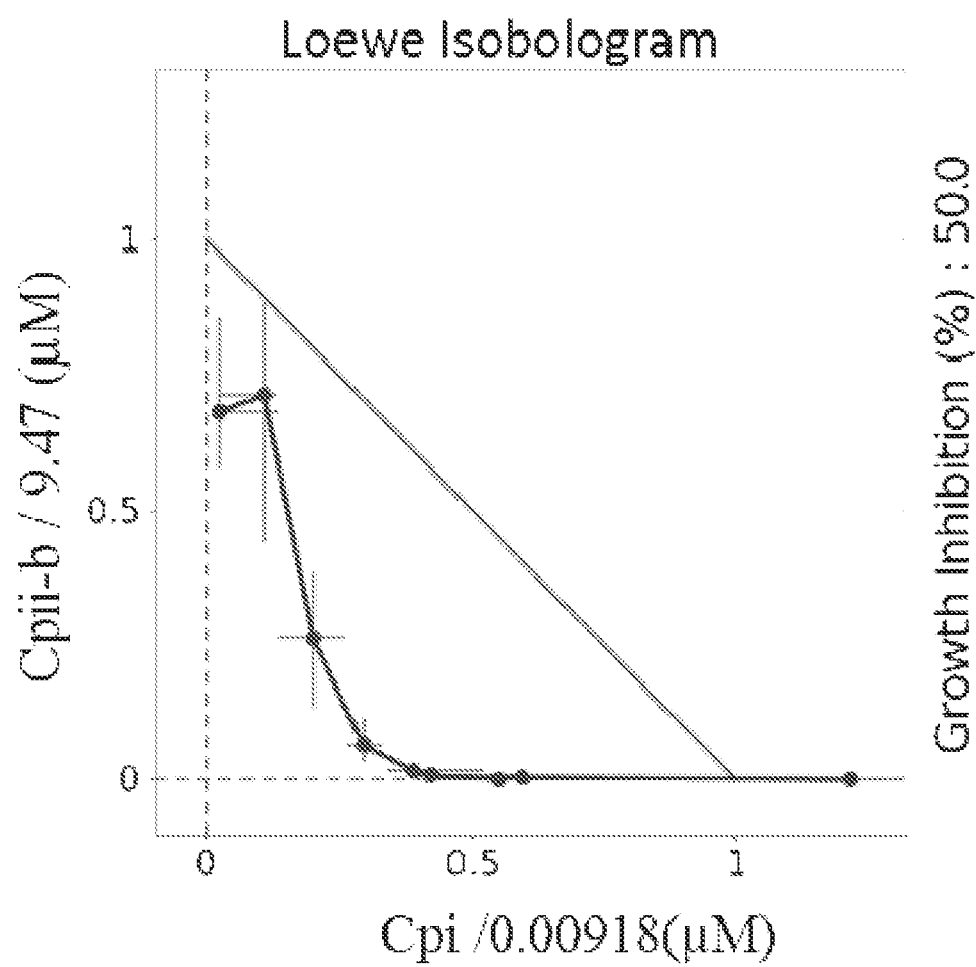

FIG. 2 illustrates the growth inhibition of HUH7 cells when treated with a concentration range of (R)-8-(6-amino-5-((2-(trifluoromethyl)pyridin-3-yl)thio)pyrazin-2-yl)-8-azaspiro[4.5]decan-1-amine (abbreviated here as CPii-b) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated here as CPi) after seven days of treatment. Percent growth inhibition (Combination Data Heatmap) and synergy assessment for checkerboard combination of the two agents across a broad concentration matrix (Loewe Excess Heatmap) or the 50% growth inhibition level (Loewe Isobologram) are shown. Synergistic combination activity is observed in a full concentration matrix with CPi and CPii-b after seven days of treatment with a combination index of 0.363.

Figure 3A:
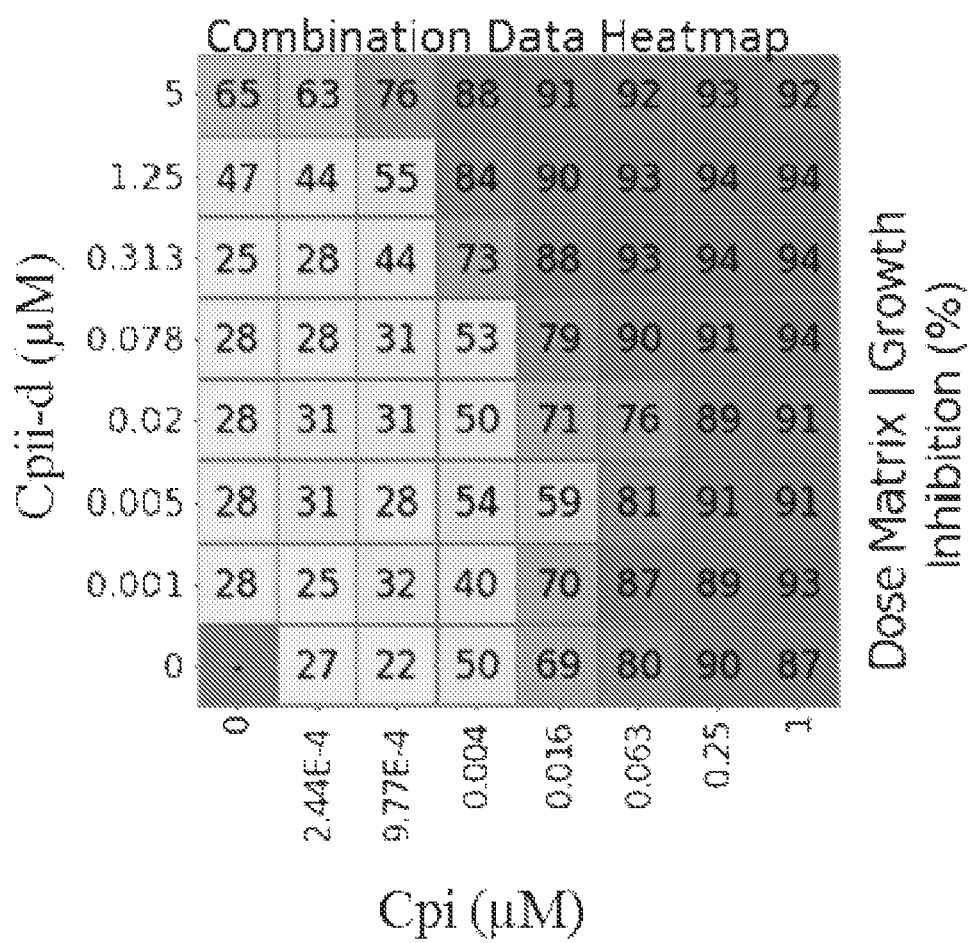
FIG. 3. Growth inhibition of HUH7 cells when treated with a concentration range of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated as CPi) and 7-Cyclopentyl-2-(5-piperazin-1-yl-pyridin-2-ylamino)-7H-pyrrolo[2,3-d]pyrimidine-6-carboxylic acid dimethylamide succinate salt (abbreviated as CPii-d) after seven days of treatment.
Figure 3B:
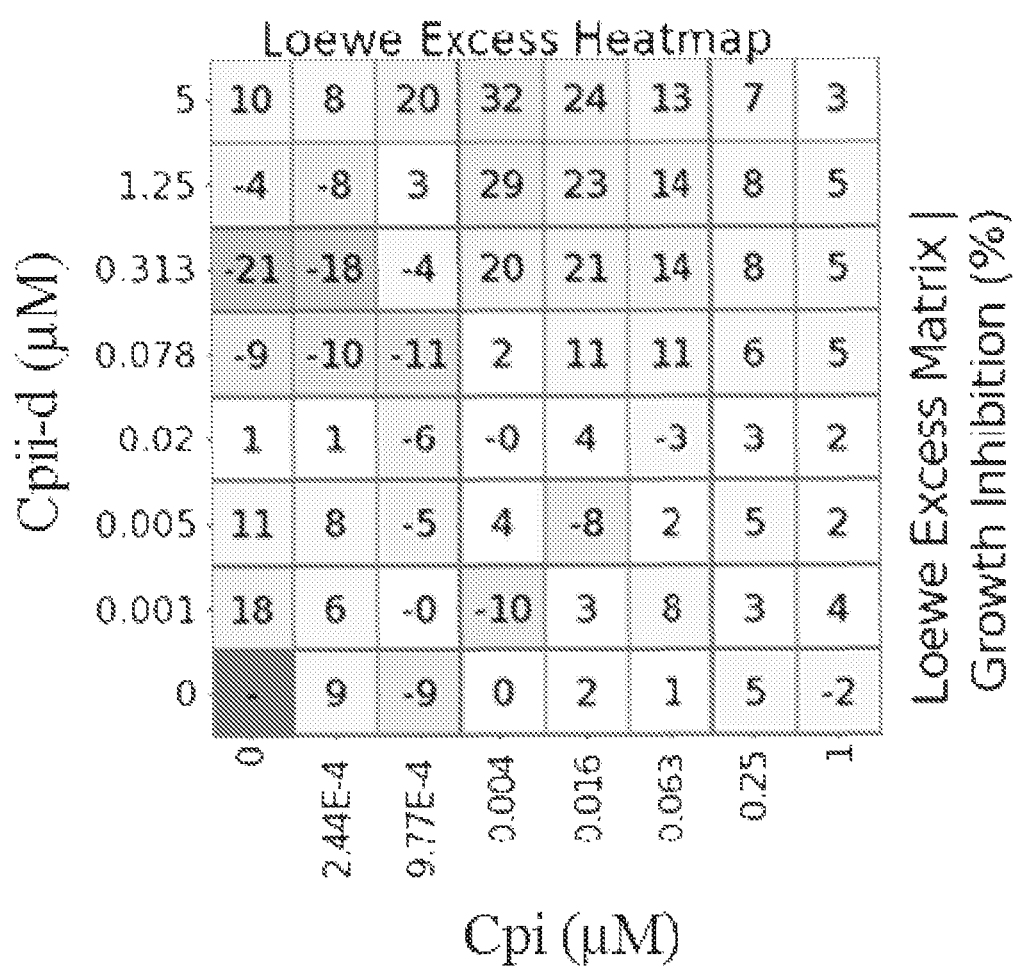
Figure 3C:
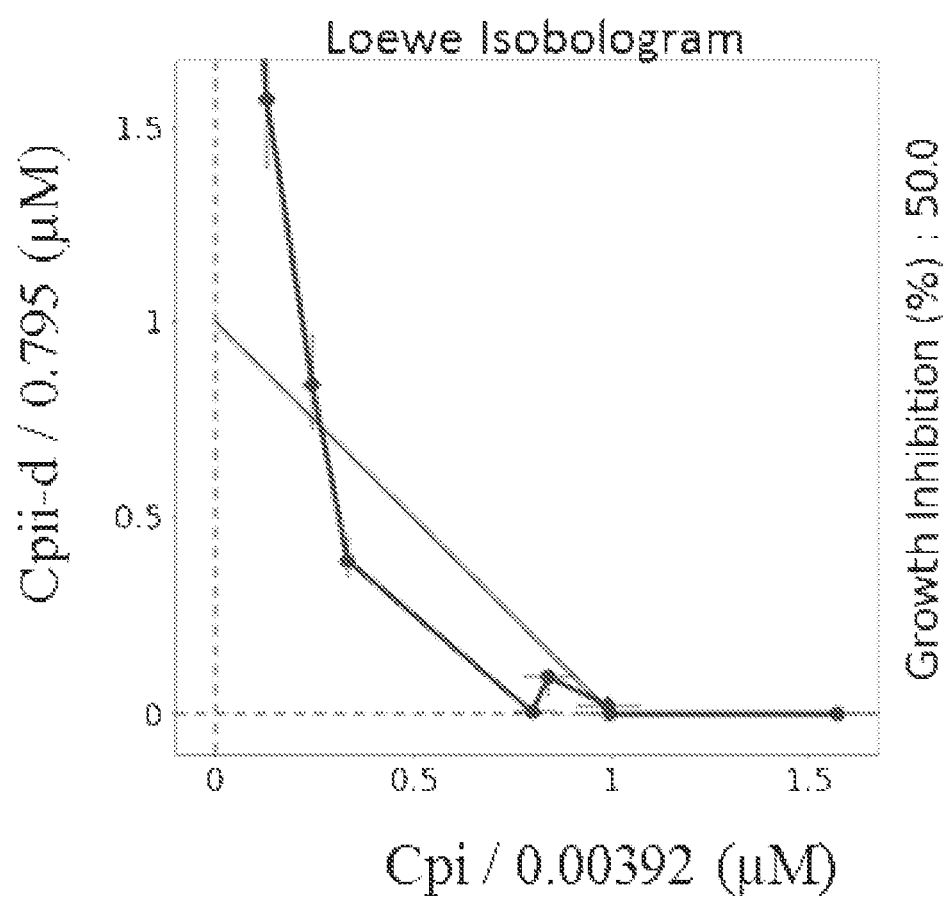

FIG. 3 illustrates the growth inhibition of HUH7 cells when treated with a concentration range of 7-Cyclopentyl-2-(5-piperazin-1-yl-pyridin-2-ylamino)-7H-pyrrolo[2,3-d]pyrimidine-6-carboxylic acid dimethylamide succinate salt (abbreviated here as CPii-d) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated here as CPi) after seven days of treatment. Percent growth inhibition (Combination Data Heatmap) and synergy assessment for checkerboard combination of the two agents across a broad concentration matrix (Loewe Excess Heatmap) or the 50% growth inhibition level (Loewe Isobologram) are shown. Synergistic combination activity is observed in a full concentration matrix with CPii-d and CPi after seven days of treatment with a combination index of 0.729.

Figure 4A:
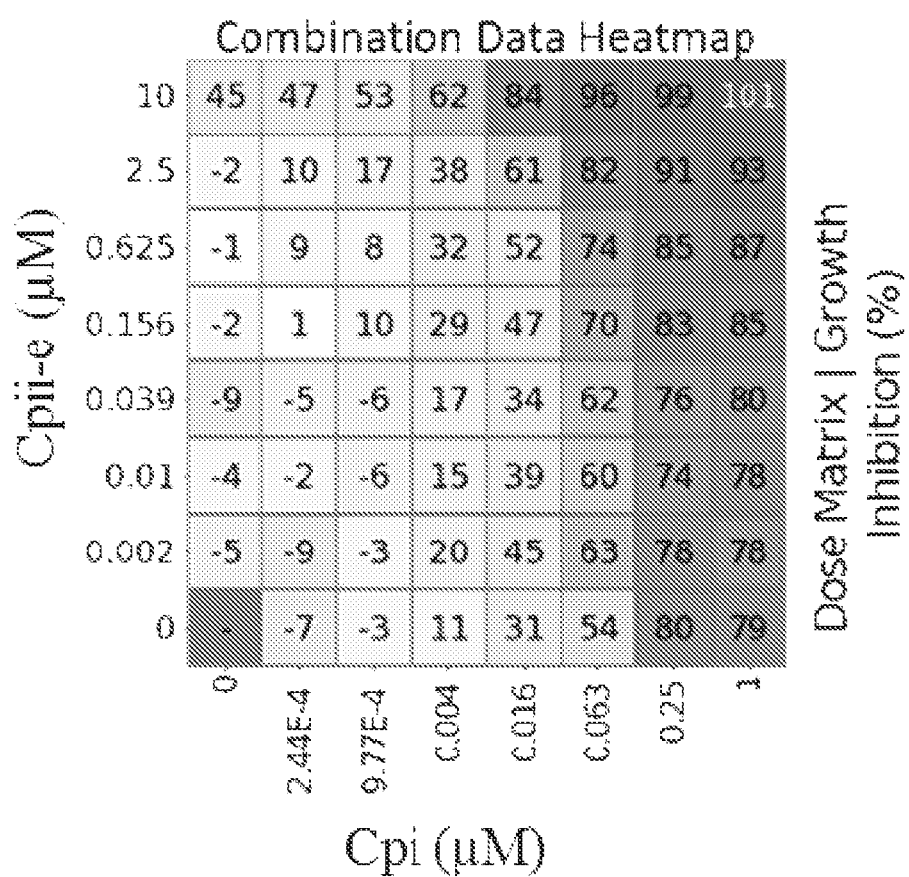
FIG. 4. Growth inhibition of HUH7 cells when treated with a concentration range of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated as CPi) and (S)-N1-(4-methyl-5-(2-(1,1,1-trifluoro-2-methylpropan-2-yl)pyridin-4-yl)thiazol-2-yl)pyrrolidine-1,2-dicarboxamide (abbreviated as CPii-e) after seven days of treatment.
Figure 4B:
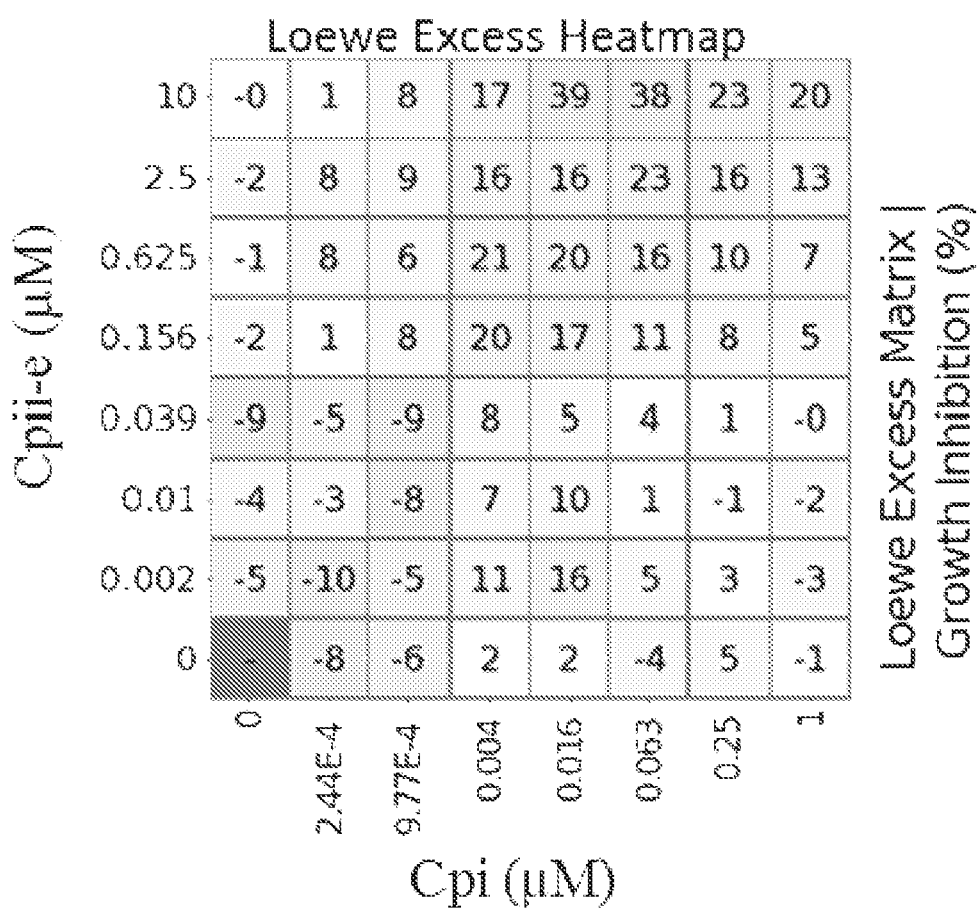
Figure 4C:
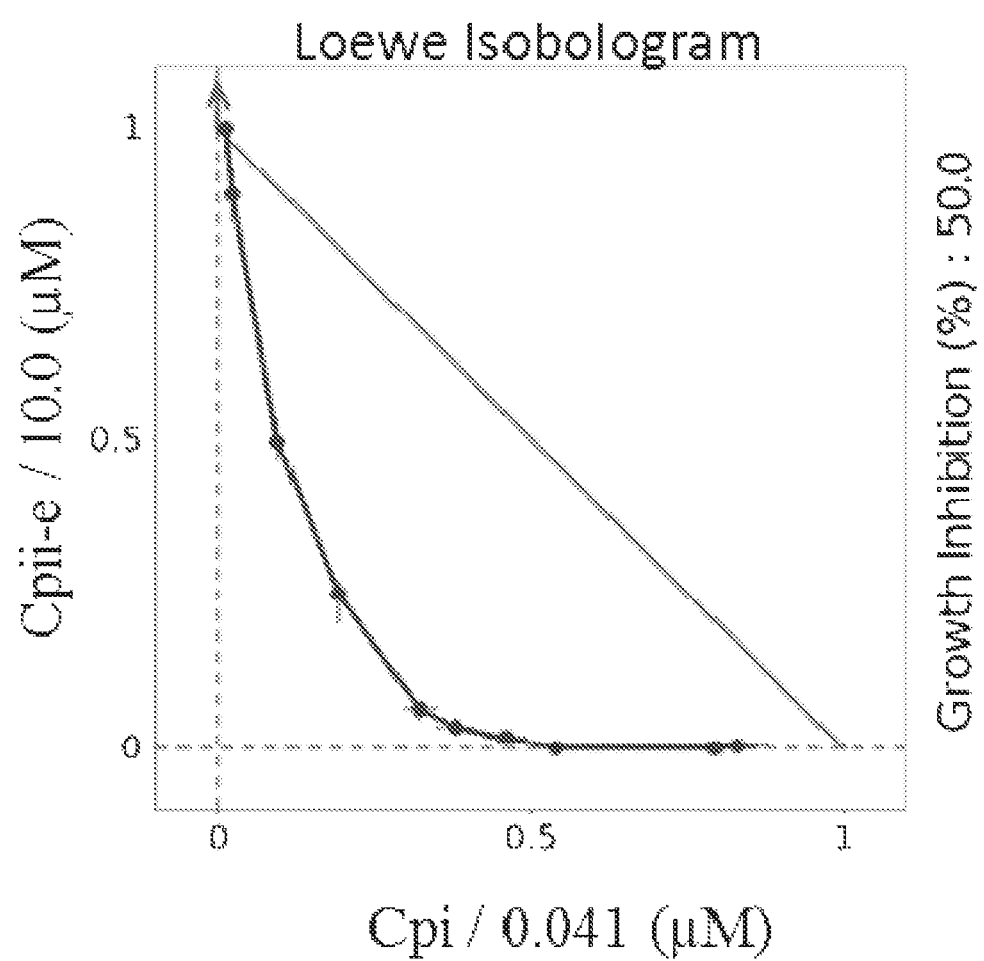

FIG. 4 illustrates the growth inhibition of HUH7 cells when treated with a concentration range of (S)-N1-(4-methyl-5-(2-(1,1,1-trifluoro-2-methylpropan-2-yl)pyridin-4-yl)thiazol-2-yl)pyrrolidine-1,2-dicarboxamide (abbreviated here as CPii-e) and N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide (abbreviated here as CPi) after seven days of treatment. Percent growth inhibition (Combination Data Heatmap) and synergy assessment for checkerboard combination of the two agents across a broad concentration matrix (Loewe Excess Heatmap) or the 50% growth inhibition level (Loewe Isobologram) are shown. Synergistic combination activity is observed in a full concentration matrix with CPi and CPii-e after seven days of treatment with a combination index of 0.385.

Figure 5A:
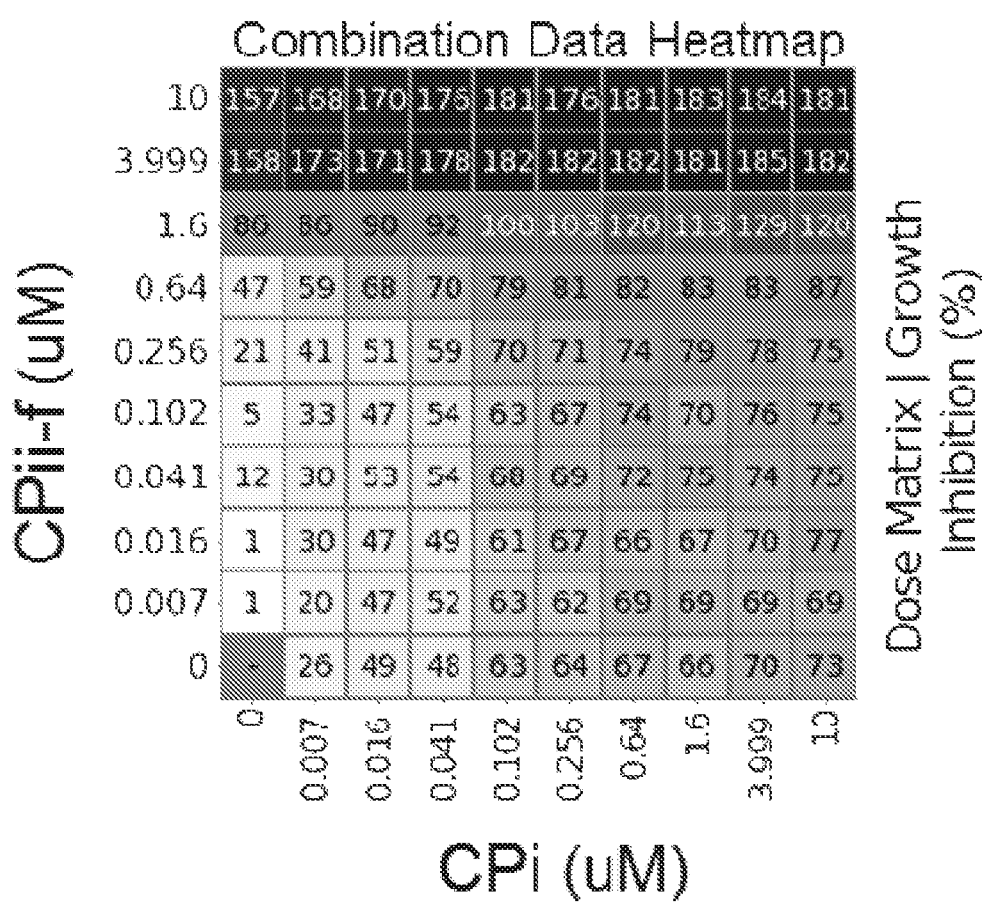
FIG. 5. Growth inhibition of HUH7 cells when treated with a concentration range of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)- carboxamide (abbreviated as CPi) and 4-(trifluoromethyl)-5-(2,6-dimorpholinopyrimidin-4-yl)pyridin-2-amine hydrochloride salt (abbreviated as CPii-f) after three days of treatment.
Figure 5B:
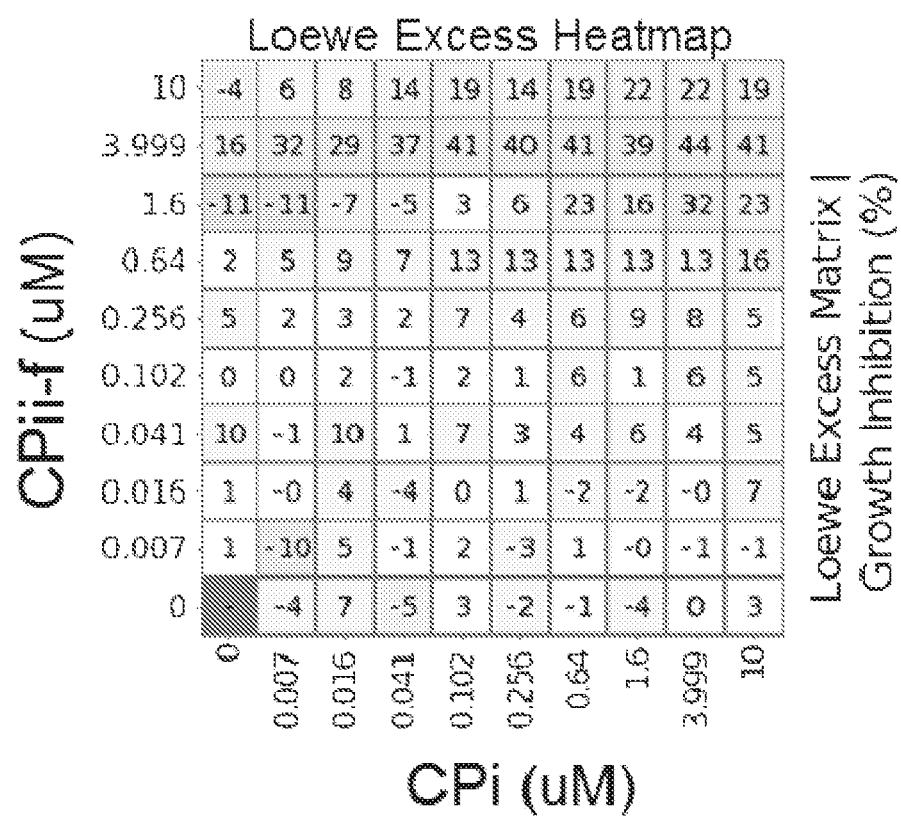
Figure 5C:
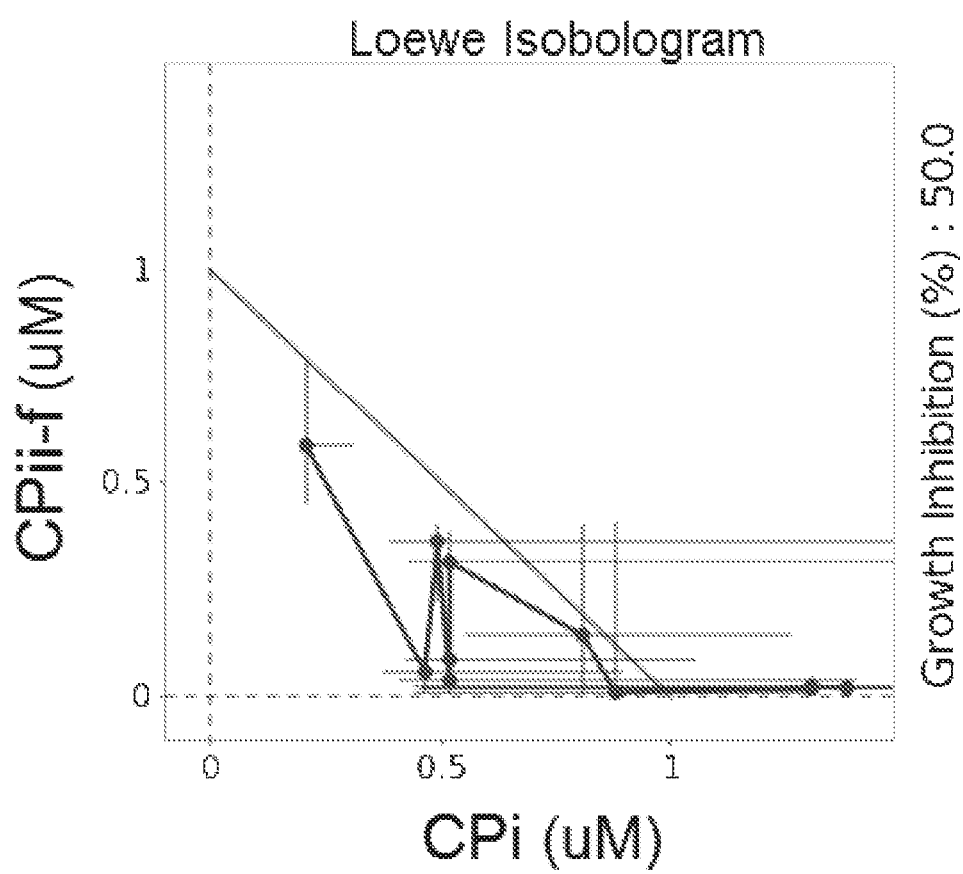

FIG. 5 illustrates the growth inhibition of HUH7 cells when treated with a concentration range of 4-(trifluoromethyl)-5-(2,6-dimorpholinopyrimidin-4-yl)pyridin-2-amine hydrochloride salt (abbreviated here as CPii-f) and N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (abbreviated here as CPi) after three days of treatment. Percent growth inhibition (Combination Data Heatmap) and synergy assessment for checkerboard combination of the two agents across a broad concentration matrix (Loewe Excess Heatmap) or the 50% growth inhibition level (Loewe Isobologram) are shown. Synergistic combination activity is observed in a full concentration matrix with CPii-f and CPi after three days of treatment with a combination index of 0.524.

Conclusions: In summary, synergistic combination activity was observed in an in vitro cell proliferation assay when CPi was combined with CPii-a, CPii-b, CPii-d, CPii-e or CPii-f.

The invention claimed is:

1. A pharmaceutical combination comprising
   (i) N-(5-cyano-4((2-methoxyethyl)amino)pyridin-2-yl)-7-formyl-6((4-methyl-2-oxopiperazin-1-yl)methyl)-3,4-dihydro-1,8-naphthyridine-1(2H)-carboxamide in free form or in pharmaceutically acceptable salt form, and
   (ii) at least one further active ingredient selected from the group consisting of
      a) 3-(2,6-dichloro-3,5-dimethoxy-phenyl)-1-{6-[4-(4-ethyl-piperazin-1-yl)-phenylamino]-pyrimidin-4-yl}-1-methyl-urea in free form or in pharmaceutically acceptable salt form;
      b) 8-(6-amino-5-((2-(trifluoromethyl)pyridin-3-yl) thio)pyrazin-2-yl)-8-azaspiro[4.5]decan-1-amine in free form or in pharmaceutically acceptable salt form;
      c) 7-Cyclopentyl-2-(5-piperazin-1-yl-pyridin-2-ylamino)-7H-pyrrolo[2,3-d]pyrimidine-6-carboxylic acid dimethylamide in free form or in pharmaceutically acceptable salt form;
      d) (S)-N1-(4-methyl-5-(2-(1,1,1-trifluoro-2-methylpropan-2-yl) pyridin-4-yl)thiazol-2-yl)pyrrolidine-1,2-dicarboxamide in free form or in pharmaceutically acceptable salt form; and
      e) 4-(trifluoromethyl)-5-(2,6-dimorpholinopyrimidin-4-yl)pyridin-2-amine in free form or in pharmaceutically acceptable salt form.

2. A pharmaceutical combination according to claim 1 comprising
   (i) the citrate salt or the free form of N-(5-cyano-4((2-methoxyethyl)amino)pyridin-2-yl)-7-formyl-6((4-methyl-2-oxopiperazin-1-yl) methyl)-3,4-dihydro-1,8-naphthyridine-1(2H)-carboxamide, and
   (ii) at least one further active ingredient selected from the group consisting of a) the monophosphate salt of 3-(2,6-dichloro-3,5-dimethoxy-phenyl)-1-{6-[4-(4-ethyl-piperazin-1-yl)-phenylamino]-pyrimidin-4-yl}-1-methyl-urea;
b) the free form of 8-(6-amino-5-((2-(trifluoromethyl)pyridin-3-yl)thio)pyrazin-2-yl)-8-azaspiro[4.5]decan-1-amine;
c) the succinate salt of 7-Cyclopentyl-2-(5-piperazin-1-yl-pyridin-2-ylamino)-7H-pyrrolo[2,3-d]pyrimidine-6-carboxylic acid dimethylamide;
d) the free form of (S)-N1-(4-methyl-5-(2-(1,1,1-trifluoro-2-methylpropan-2-yl)pyridin-4-thiazol-2-yl)pyrrolidine-1,2-dicarboxamide; and
e) the hydrochloride salt of 4-(trifluoromethyl)-5-(2,6-dimorpholinopyrimidin-4-yl)pyridin-2-amine.

3. A pharmaceutical combination according to claim 1 further comprising at least one pharmaceutically acceptable carrier.

4. A pharmaceutical composition comprising a combination as defined in claim 1 and at least one pharmaceutically acceptable carrier.

5. A commercial package comprising a pharmaceutical combination as defined in claim 1 together with instructions for simultaneous or sequential administration thereof for use in the delay of progression or treatment of a proliferative disease.

6. A pharmaceutical combination according to claim 2 further comprising at least one pharmaceutically acceptable carrier.

7. A pharmaceutical composition comprising a combination as defined in claim 2 and at least one pharmaceutically acceptable carrier.

* * * * *